(12) United States Patent
Ghoshal et al.

(10) Patent No.: US 7,781,570 B2
(45) Date of Patent: Aug. 24, 2010

(54) SITE-SPECIFIC AMINOGLYCOSIDE DERIVATIVES FOR USE IN IMMUNODIAGNOSTIC ASSAYS

(75) Inventors: Mitali Ghoshal, Noblesville, IN (US); Salvatore J. Salamone, Stockton, NJ (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 523 days.

(21) Appl. No.: 11/675,216

(22) Filed: Feb. 15, 2007

(65) Prior Publication Data

US 2007/0148700 A1 Jun. 28, 2007

Related U.S. Application Data

(62) Division of application No. 10/624,822, filed on Jul. 22, 2003, now Pat. No. 7,235,370, which is a division of application No. 09/920,402, filed on Jul. 31, 2001, now Pat. No. 6,653,456.

(51) Int. Cl.
*C07K 16/00* (2006.01)
*C07K 1/04* (2006.01)

(52) U.S. Cl. ............ 530/389.8; 530/403; 530/807
(58) Field of Classification Search .............. None
See application file for complete search history.

(56) References Cited

U.S. PATENT DOCUMENTS

| 4,447,529 | A | * | 5/1984 | Greenquist et al. | 435/7.7 |
| 4,548,908 | A | * | 10/1985 | Kameda | 436/500 |
| 2002/0106654 | A1 | * | 8/2002 | Kojima | 435/6 |

* cited by examiner

*Primary Examiner*—Shafiqul Haq

(57) ABSTRACT

A method of making a derivatized aminoglycoside includes reacting an aminoglycoside with at least 2 equivalents of a divalent metal ion in an aprotic solvent to complex two neighboring amino group and hydroxyl group pairs; reacting the non-complexed amino groups with a protecting reagent to provide protecting groups; removing the divalent metal ion to provide two unprotected amino groups; reacting one of the unprotected amino groups with a reactive substance containing an linker, a carrier, or a label; and removing the protecting groups. This method can be used to produce novel compounds and regents.

2 Claims, 30 Drawing Sheets

SITE-SPECIFIC AMINOGLYCOSIDE DERIVATIVES FOR USE IN IMMUNODIAGNOSTIC ASSAYS

RELATED APPLICATIONS

This application is a division of U.S. Ser. No. 10/624,822 filed Jul. 22, 2003 now U.S. Pat. No. 7,235,370, which is a division of U.S. Ser. No. 09/920,402 filed Jul. 31, 2001, which issued as U.S. Pat. No. 6,653,456 on Nov. 25, 2003.

BACKGROUND OF THE INVENTION

Aminoglycosides are a family of highly potent, broad-spectrum antibiotics which can be used to treat infections caused by gram-negative as well as gram-positive bacteria. However, these antibiotics have a narrow therapeutic index and are potentially nephrotoxic and ototoxic. (M. Jolley, et al., *Clin. Chem.* 27(7), 1190-1197 (1981); U.S. Pat. No. 5,079,234.) Consequently, it is desirable for patients treated with aminoglycosides to be under close clinical observation to guide the safe therapeutic use of these antibiotics. An effective tool in the guidance is the monitoring of aminoglycoside concentration in the biological fluid of a treated patient, and there is a continuing effort to improve the performance and sensitivity of assays for aminoglycoside antibiotics.

In testing for analytes such as drug molecules (including aminoglycosides), immunoassays, particularly competitive binding immunoassays, have proven to be especially advantageous. In competitive binding immunoassays, an analyte in a biological sample competes with a labeled reagent, also known as an analyte analog or tracer, for a limited number of receptor binding sites on antibodies specific for the analyte and analyte analog. Enzymes such as β-galactosidase and peroxidase, fluorscent molecules such as fluorescein compounds, radioactive compounds such as $^{125}I$, and microparticles are common labeling substances used in tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

The modification of aminoglycosides for use as well dell defined tracers in immunoassays can be problematic. The synthesis of aminoglycoside tracers typically yields a mixture of products, rather than site-specific derivatives due to the presence of multiple amino (N—H) functionalities (U.S. Pat. Nos. 5,849,599; 4,816,391; 4,328,311; Mallams, J. C. S. *Perkins I*, 1981, 2186-2208.) The desired product is difficult to separate from the mixture and cannot typically be characterized as a single product. This uncertainty leads to poor reproducibility of the synthesis and consequently to variations in product quality. Also, any further manipulations or modifications of the product are difficult, since the presence of unwanted products (side products) may interfere with the desired product. Variations in product quality can cause the analysis to have different characteristics for different batches of the tracer, thus requiring the user to calibrate the analysis each time a different batch of tracer is used.

It is thus desirable to provide aminoglycoside derivatives which can be easily isolated as pure, single products. It is also desirable to be able to modify the aminoglycosides to increase their utility under a wider variety of assay conditions.

SUMMARY OF THE INVENTION

In one aspect of the invention, there is a method of making a derivatized aminoglycoside comprising reacting an aminoglycoside of formula (I) with at least 2 equivalents of a divalent metal ion in an aprotic solvent to complex two neighboring amino group and hydroxyl group pairs:

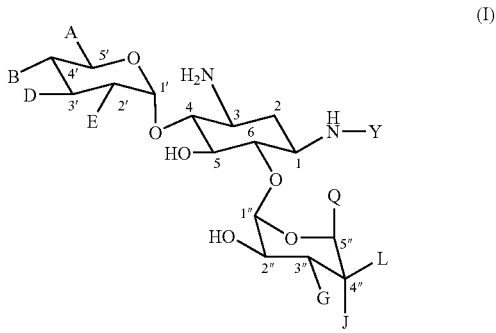

(I)

wherein A is $CH_2NH_2$, $CHCH_3NH_2$, or $CHCH_3NHCH_3$; B is H or OH; D is H or OH; E is $NH_2$ or OH; G is $NH_2$ or $NHCH_3$; J is H or OH; L is H, $CH_3$, or OH; Q is H or $CH_2OH$; and Y is H or $C(=O)CH(OH)CH_2CH_2NH_2$; reacting the non-complexed amino groups with a protecting reagent to provide protecting groups; removing the divalent metal ion to provide two unprotected amino groups; reacting one of the unprotected amino groups with a reactive substance comprising T; and removing the protecting groups to produce a compound of formula (II):

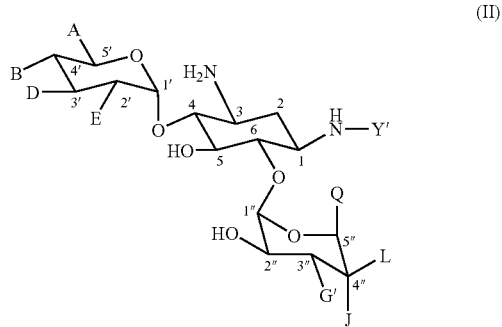

(II)

wherein G' is $NH_2$, $NHCH_3$, NH-T, or $NCH_3$-T; Y' is H, $C(=O)CH(OH)CH_2CH_2NH_2$, or T; and T is a linker group, a carrier, or a label.

In another embodiment of the invention, there is a reagent for an assay comprising a compound of formula (II):

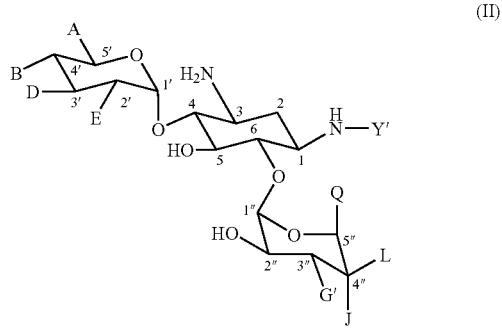

(II)

wherein A is CH$_2$NH$_2$, CHCH$_3$NH$_2$, or CHCH$_3$NHCH$_3$; B is H or OH; D is H or OH; E is NH$_2$ or OH; G' is NH$_2$, NHCH$_3$, NH-T, or NCH$_3$-T; J is H or OH; L is H, CH$_3$, or OH; Q is H or CH$_2$OH; and Y' is H, C(=O)CH(OH)CH$_2$CH$_2$NH$_2$ or T; T is a linker group, a carrier, or a label; and T is present in only one of G' or Y'; and wherein the purity of the compound is at least 90%.

In yet another embodiment of the invention, there is an antibody produced in response to the above reagent.

In yet another embodiment of the invention, there is an assay method for determining an aminoglycoside comprising combining a sample suspected of containing said aminoglycoside with an antibody specific for said aminoglycoside and with the above reagent, the reagent comprising the analyte analog of said aminoglycoside, and the reagent capable of forming a detectable complex with said antibody; and determining the presence or amount of said detectable complex as a measure of said analyte in said sample.

In yet another embodiment of the invention, there is an assay method for determining an aminoglycoside comprising combining a sample suspected of containing said aminoglycoside with a reagent and with the above antibody, the reagent comprising an analyte analog of said aminoglycoside, and the reagent capable of forming a detectable complex with said antibody; and determining the presence or amount of said detectable complex as a measure of said analyte in said sample.

In yet another embodiment of the invention, there is a compound of formula (II):

(II)

wherein A is CH$_2$NH$_2$, CHCH$_3$NH$_2$, or CHCH$_3$NHCH$_3$; B is H or OH; D is H or OH; E is NH$_2$ or OH; G' is NH$_2$, NHCH$_3$, NH—X, or NCH$_3$—X; J is H or OH; L is H, CH$_3$, or OH; Q is H or CH$_2$OH; and Y' is H, C(=O)CH(OH)CH$_2$CH$_2$NH$_2$, or X; and wherein X is present in only one of G' or Y' and is a moiety of formula (VIII), (IX), or (X):

(VIII)

(IX)

(X)

In yet another embodiment, there is a test kit comprising the above reagent, the above compound, or the above antibody.

DETAILED DESCRIPTION OF THE INVENTION

Figure 1:
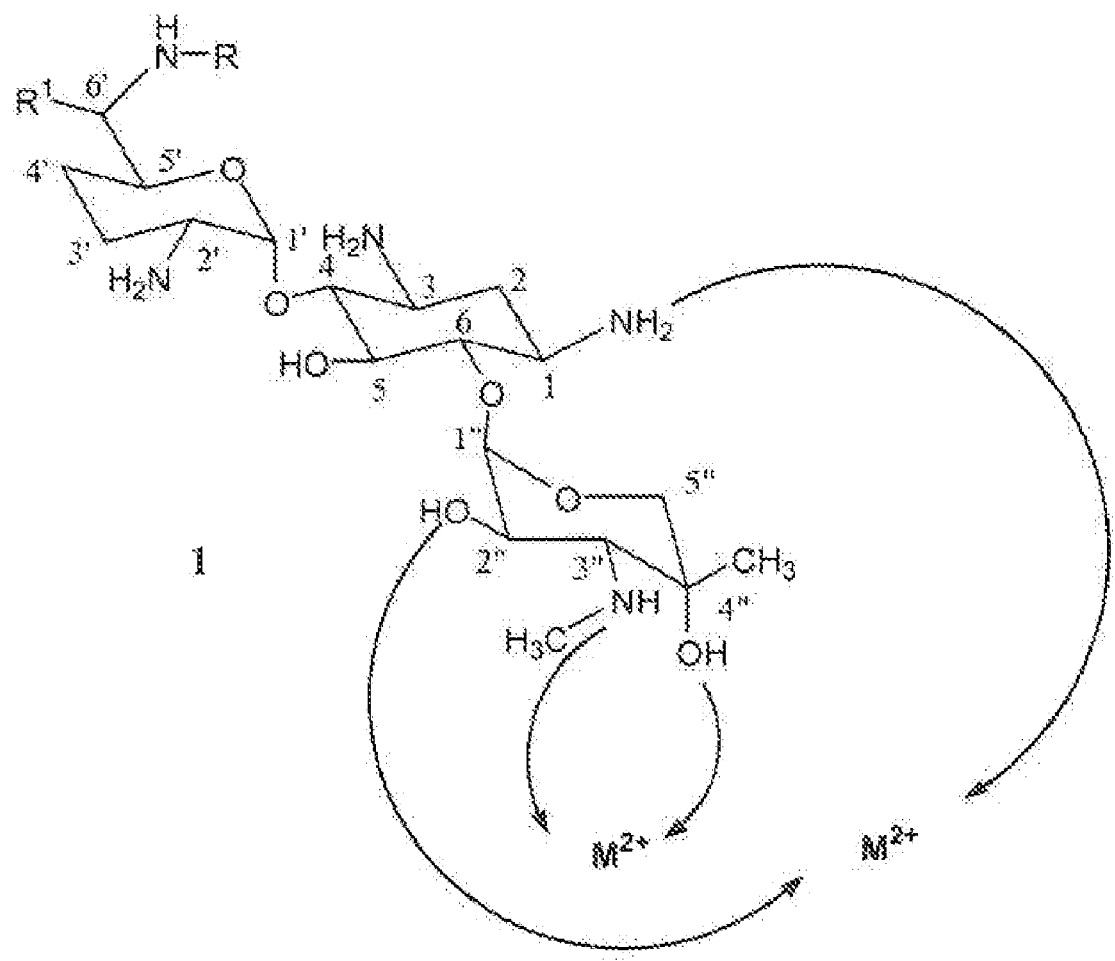
FIG. 1 is an illustration of the metal complex protecting group.

The present invention relates generally to methods of making site-specific aminoglycoside derivatives, and more particularly to providing these derivatives without substantial amounts of derivatives which are non-site specific. Aminoglycoside derivatives made in accordance with the present invention have greater utility due to the decreased abundance of derivatives which do not have the desired modification. The present invention also relates to methods of using aminoglycoside derivatives in assays, as well as to specific aminoglycoside derivatives which are useful in these assays.

The most prevalent aminoglycosides used in clinical practice are the gentamicins, kanamycins, amikacin, and tobramycin, all of which have a pseudotrisaccharidic structure containing a diaminocyclitol unit and two amino sugar units. Derivatives of these drugs, also known as analyte analogs, can be used in assays to determine the presence or amount of the drug (analyte) in a sample. Typically, these derivatives contain a linking group which bonds or conjugates the derivative to another substance, referred to as a label. The combination of the drug and label is typically referred to as a tracer.

"Analyte" refers to the substance, or group of substances, whose presence or amount thereof in a liquid medium is to be determined including, but not limited to, any drug or drug derivative, hormone, protein antigen, or oligonucleotide.

"Analyte analog" means any substance or group of substances which behaves essentially the same as the analyte with respect to binding affinity of the antibody for the analyte including, but not limited to, any aminoglycoside or derivative and metabolites and isomers thereof.

"Antibody" or "receptor" means a specific binding partner of the analyte and is meant to include any substance or group of substances which has a specific binding affinity for the analyte to the exclusion of other substances. The term includes polyclonal antibodies, monoclonal antibodies, and antibody fragments.

Haptens are partial or incomplete antigens. They are substance, typically of low molecular weight, which are not capable of stimulating antibody formation but which do react with antibodies. The latter are formed by coupling the hapten to a high molecular weight carrier and injecting this coupled product into humans or animals. Examples of haptens include therapeutic drugs such as digoxin and theophylline, drugs of abuse such as morphine and LSD, antibiotics such as aminoglycosides and vancomycin, hormones such as estrogen and progesterone, vitamins such as vitamin B12 and folic acid, thyoxin, histamine, serotonin, adrenaline, and others.

An "activated hapten" refers to a hapten derivative that has been provided with an available site for reaction, such as by the attachment of a linking group for synthesizing a derivative conjugate.

A "carrier" refers to an immunogenic substance, commonly a protein, that can join with a hapten, thereby enabling the hapten to stimulate an immune response. Carrier substances include proteins, glycoproteins, complex polysaccharides, and nucleic acids that are recognized as foreign and thereby elicit an immunologic response from the host.

The terms "immunogen" and "immunogenic" refer to substances capable of producing or generating an immune response in an organism.

The term "derivative" refers to a chemical compound or molecule made from a parent compound or molecule by one or more chemical reactions.

"Protecting group" refers to a moiety formed by the reaction of a protecting reagent with a functional group such as NH, $NH_2$, or OH on a compound. The protecting group is stable to chemical environments which modify other moieties on the compound yet can be controllably removed to provide the original functional group.

Linking groups are used to activate, i.e., to provide an available site on a drug derivative for synthesizing a hapten. The use of a linking group may or may not be advantageous or needed, depending on the specific hapten and carrier pairs. The term "linker" refers to a chemical moiety that connects a hapten to a carrier, immunogen, label, tracer, or another linker. Linkers may be straight or branched, saturated or unsaturated carbon chains, optionally containing aromatic or non-aromatic rings. They may also include one or more heteroatoms within the chain or at the termini of the chains. The term "heteroatom" is meant to include atoms other than carbon which are chosen from the group consisting of oxygen, nitrogen, sulfur, and phosphorus.

A detector molecule, or label, is an identifying tag which, when attached to a carrier substance or molecule, can be used to detect an analyte. A label may be attached to its carrier substance or antibody directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, radioactive isotopes such as $^{125}I$, and polymers such as dextran and its derivatives.

The term "active ester" encompasses ester groups which can react with free amino groups of peptides under such conditions that no interfering side reactions occur with other reactive groups of the peptide. An N-hydroxysuccinimide ester is preferably used as the active ester. Analogous p-nitrophenyl, pentafluorophenyl, imidazolyl, or N-hydroxybenzotriazolyl esters can also be used in addition to N-hydroxysuccinimide esters.

A peptide is any compound formed by the linkage of two or more amino acids by amide (peptide) bonds, usually a polymer of α-amino acids in which the α-amino group of each amino acid residue (except the $NH_2$ terminal) is linked to the α-carboxyl group of the next residue in a linear chain. The terms "peptide," "polypeptide," and poly(amino acid) are used synonymously herein to refer to this class of compounds without restriction as to size. The largest members of this class are referred to as proteins.

Any sample that is suspected of containing the analyte, i.e., an aminoglycoside, can be analyzed by the method of the present invention. The sample is typically an aqueous solution such as a body fluid from a host, for example, urine, whole blood, plasma, serum, saliva, semen, stool, sputum, cerebral spinal fluid, tears, mucus, and the like, but preferably is plasma or serum. The sample can be pretreated if desired an can be prepared in any convenient medium that does not interfere with the assay. An aqueous medium is preferred.

Figure 15:
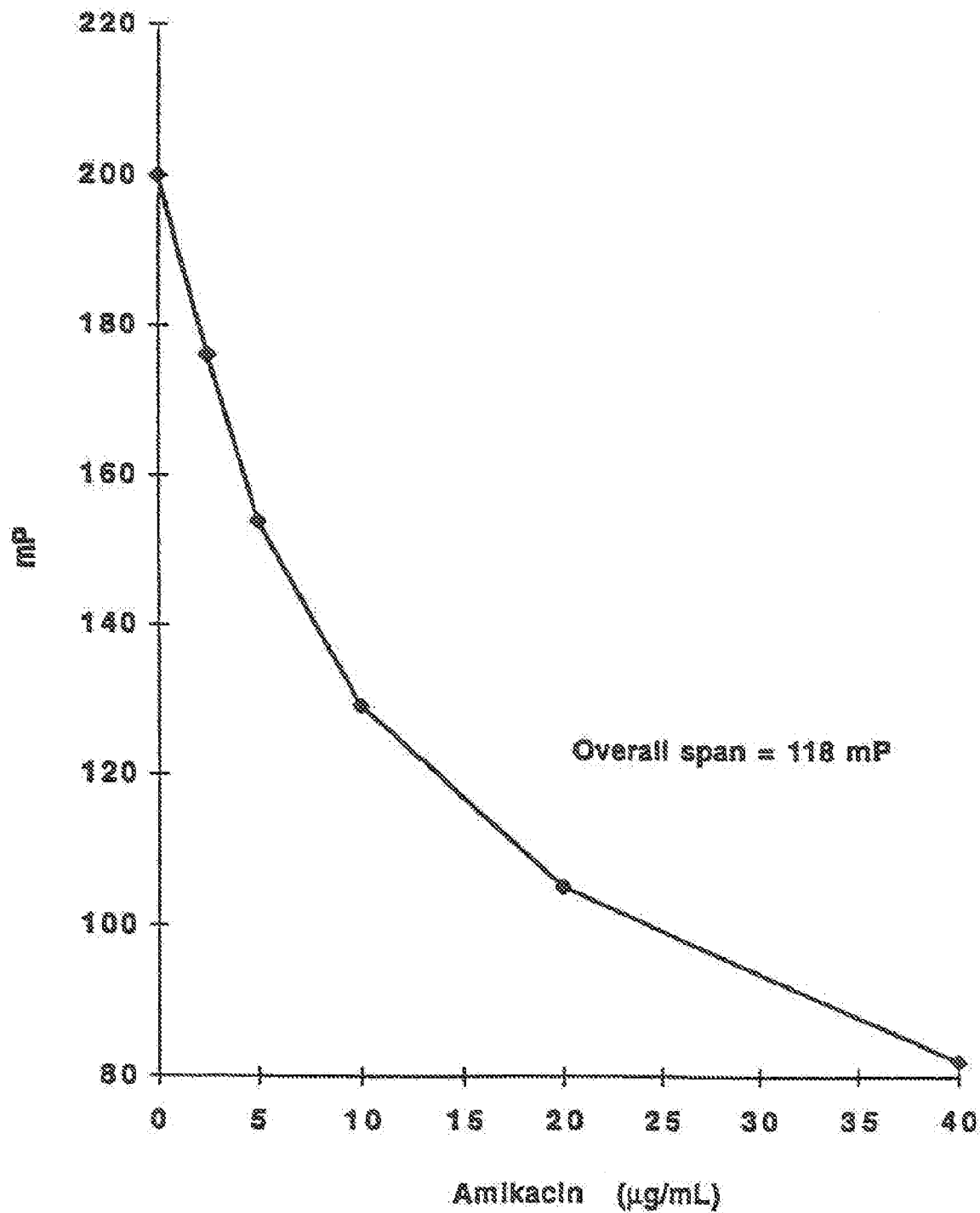
FIG. 15 is a graph showing standard (dose response) curves generated from data using conjugates and antibodies of amikacin in a fluorescence polarization immunoassay.
Figure 22:
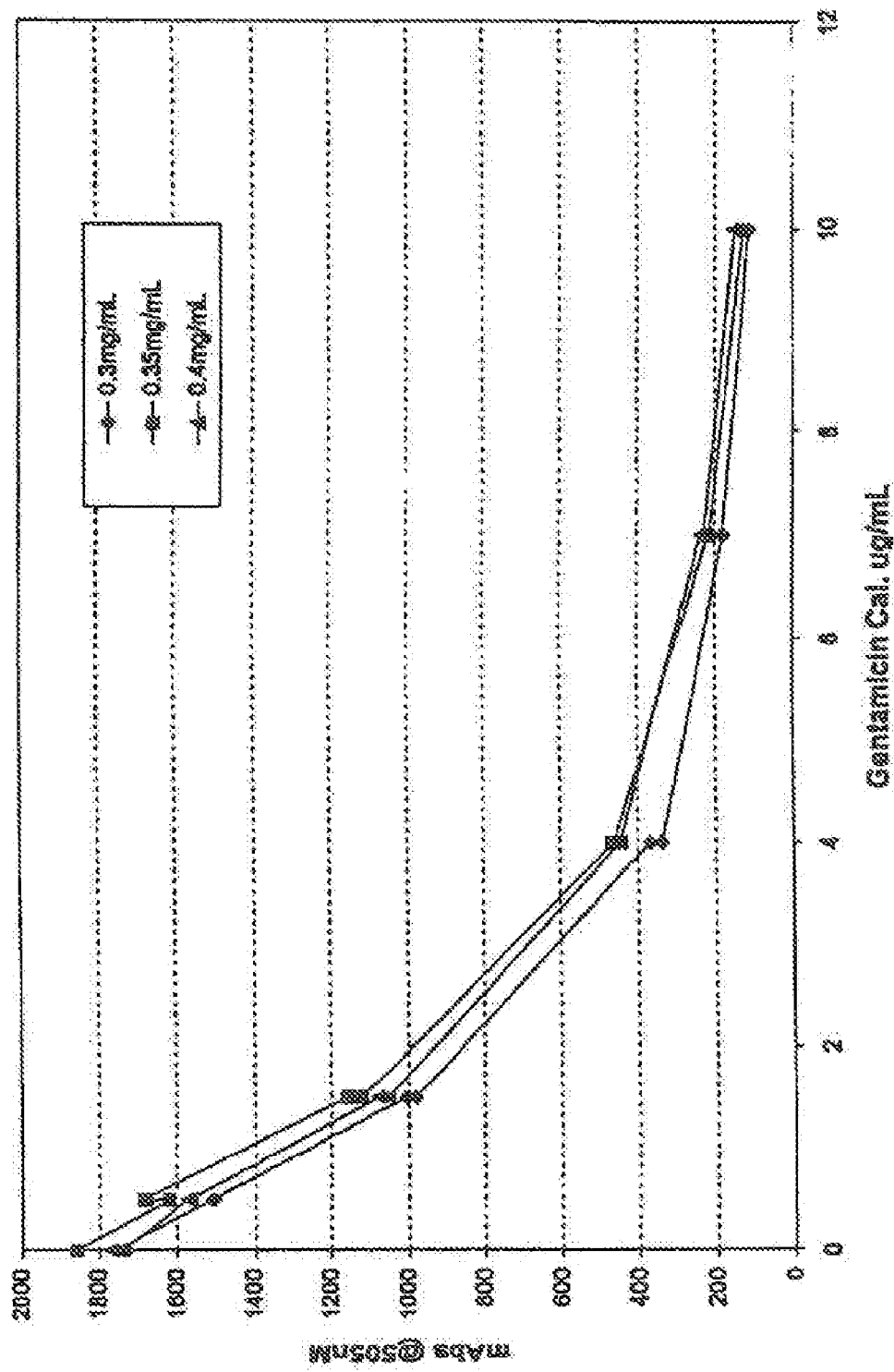
FIG. 22 is a graph showing standard (dose response) curves generated from data using conjugates and antibodies of gentamicin in a KIMS immunoassay.

"Calibration material" means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard. This comparison is aided by the construction of a calibration curve as illustrated in FIGS. 15 and 22.

A variety of methods may be used for performing immunoassay of aminoglycosides. Two of the more practical assays are those based on fluorescence polarization (FP) and those based on kinetic interaction of microparticles in solution (KIMS). Both of these methods require the site selective modification of the aminoglycoside. In the case of KIMS, the aminoglycoside is conjugated to a polymer label such as dextran or to a poly(amino acid). In the case of FP assays, the aminoglycoside is modified with a fluorescein label.

It is typically very difficult to provide aminoglycoside derivatives which have been modified at a single site on the molecule without side products. For example, aminoglycoside FP tracers can be made from an aminoglycoside by reaction of fluorescein with an amino group on the aminoglycoside (U.S. Pat. Nos. 5,858,805 and 4,977,077). Typically, this reaction results in a distribution of products, since the label can react with more than one amino group on a particular aminoglycoside (Jolley et al., *Clin. Chem.* 27(7), 1190-1197, 1981). It is preferable first to modify the aminoglycoside so as to protect all the amino groups except for the one amino group of interest. This approach, however, can also be difficult in that a distribution of protected products is typically obtained when using conventional protection techniques. The desired product having only a single unprotected amino functionality can be difficult to purify.

The present invention provides a method of modifying aminoglycosides in a site selective manner. That is, aminoglycoside derivatives having a discrete structure, rather than a distribution of products, can be made by a process of selective protection and deprotection of the amino groups on the aminoglycoside. This process in general includes the complexation of neighboring amino and hydroxyl groups by divalent metal ions, the protection of amino groups which are not complexed by the divalent metal ion, the removal of the divalent metal ion, and the selective protection and/or modification of the amino groups which are previously complexed by the metal ion.

Certain amino groups of aminoglycosides can be selectively protected by complexation with a divalent metal cation. A divalent metal cation such as copper (Cu), nickel (Ni), cobalt (Co), zinc (Zn), or cadmium (Cd), when mixed with an aminoglycoside in an aprotic solvent, can form a complex between an amino group and a neighboring hydroxyl (—OH) group. This is described in U.S. Pat. Nos. 4,230,847 and 4,337,335, which are incorporated herein by reference. An available neighboring amino group and hydroxyl group pair is defined as: (a) an amino group and a hydroxyl group which are attached to adjacent carbon atoms and are in a cis-vicinal or diequatorial trans-vicinal orientation or (b) an amino group and a hydroxyl group which are in proximity to each other sufficient to allow for hydrogen-bonding between the two groups.

A neighboring amino group and hydroxyl group pair thus has an amino group and a hydroxyl group in an orientation and proximity which allow for the amino group and the hydroxyl group together to form a complex with a divalent metal ion. This technique of selective complexation has been described as a step in a method that provides aminoglycosides having reduced toxicity (Van Schepdael, *J. Med. Chem.* 34, 1483-1492, 1991).

This protection is illustrated in FIG. 1 for a generic structure of gentamicin. For gentamicin $C_1$, R=$CH_3$ and $R^1$=$CH_3$. For gentamicin $C_2$, R=H and $R^1$=$CH_3$. For gentamicin $C_{1a}$, R=H and $R^1$=H. The symbol $M^{2+}$ refers to $Cu^{2+}$, $Co^{2+}$, $Ni^{2+}$, $Zn^{2+}$, or $Cd^{2+}$. One equivalent of the divalent metal ion is believed to complex with the —$NH_2$ group on the C-1 position and the —OH group on the C-2" position. A second equivalent of the divalent metal ion is believed to complex the —NHR group on the C-3" position and the —OH group of the C-4" position. The unprotected amino groups in complex 1 in FIG. 1 may then be protected with a standard protecting group, preferably an acyl group (—C(=O)R). Protection of amino groups is described in Greene, *Protective Groups in Organic Synthesis*, Wiley & Sons. 1991.

Figure 2:
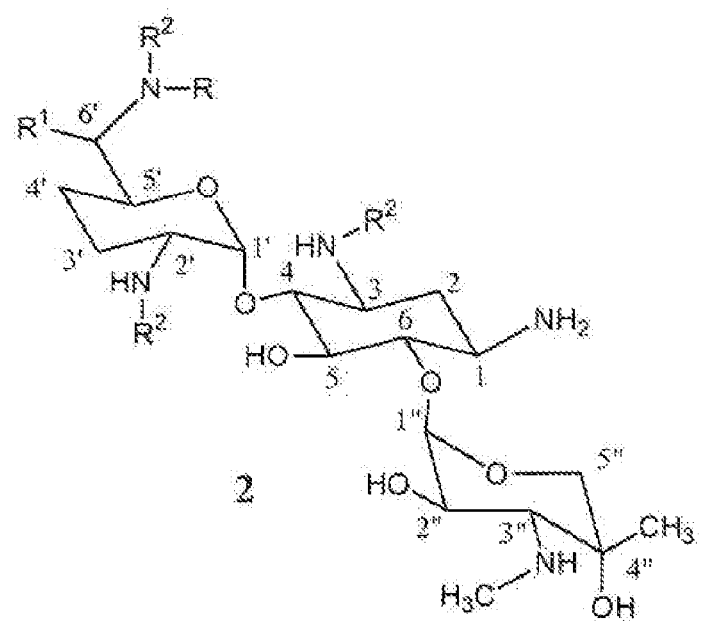
FIG. 2 is an exemplary structure of an aminoglycoside having two unprotected amino groups.
Figure 3:
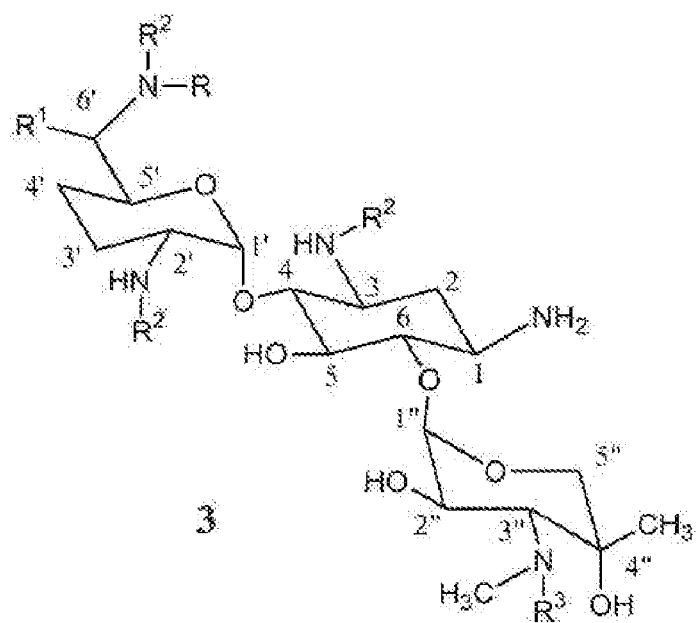
FIG. 3 is an exemplary structure of an aminoglycoside having one unprotected amino group.

Removal of the metal ion then provides a structure similar to species 2 in FIG. 2. The metal ion may be removed by treatment with ammonium hydroxide or by precipitation, for example, by treatment with a sulfide reagent. This removal provides two unprotected amino groups, one of which (C-3") is in a vicinal orientation with a hydroxyl group (C-2" and/or C-4"). The amine which is vicinal to a hyroxyl group can then be selectively protected, leaving the amino group on the C-1 position. This provides a structure similar to species 3 in FIG. 3. The remaining unprotected amino group can then be used to couple the molecule to another substance to yield a tracer. Once the molecule has been converted into the tracer, the protecting groups can be removed, restoring the binding functionality of the original molecule. The protecting groups may also be removed selectively, depending on the original molecule and on the conditions employed. In this way, multiple modifications can be performed on a single molecule.

Typically the molar quantity of transition metal salt used in at least equal to the molar quantity of the aminoglycoside multiplied by the number of available, neighboring amino group and hydroxyl group pairs within the molecule. Transition metal salts useful as complexing agents include any divalent salt of copper (II), nickel (II), cobalt (II), zinc (II), and cadmium (II). Among those which have the strongest complexing activity are divalent transition metal salts of weak acids, especially weak organic acids such as benzoic, propionic, and acetic acid. Preferred divalent transition metal salts includes the acetate salt of copper (II), nickel (II), cobalt (II), zinc (II), and cadmium (II) and mixtures thereof.

The protection of the non-complexed amino groups may be accomplished by standard methods. Although the protecting groups may be formed from a variety of protecting reagents, it is preferred that the protecting groups formed with the amino groups are stable to the conditions used in subsequent modifications. The protecting groups should remain intact and bound to the amino groups until they are removed using the appropriate deprotection methods.

Typically, the molar quantity of acylating agent used is about equal to the molar quantity of the aminoglycoside times the number of non-complexed amino functions in the molecule which are to be protected. When there is a difference in the reactivity of the non-complexed amines, one may use less N-acylating reagent if one desires to N-acylate only the more reactive amines.

The acyl protecting groups and the corresponding acylating reagents from which they are formed are well known in the art, as are methods for their removal after a desired chemical transformation has been carried out at some other site in the molecule. Acyl protecting groups which may be selectively introduced onto non-complexed amino functions in an aminoglycoside-transition metal salt complex intermediate may include the following: benzyloxycarbonyl and substituted benzyloxycarbonyl groups such as p-nitrobenzyloxycarbonyl and p-methoxybenzyloxycarbonyl (which may be removed by catalytic reduction); aryloxycarbonyl groups such as phenoxycarbonyl; alkoxycarbonyl groups such as methoxycarbonyl, ethoxycarbonyl and the like (which are preferentially removed by basic hydrolysis); trichloroethoxycarbonyl groups (removable by zinc in acetic acid); tertiary-alkoxycarbonyl groups such as tert-butoxycarbonyl and tertamyloxycarbonyl groups (removable by mild acid hydrolysis); halogenoalkylcarbonyl groups such as chloroacetyl (removable with base or with thiourea or a similar reagent) and trifluoroacetyl (removable under mild basic conditions); succinimido and phthalimido groups (removable by treatment with hydrazine); and alkanoyl groups such as acetyl, propionyl, and the like, as well as aroyl groups such as benzoyl (which are removed by basic hydrolysis).

Aminoglycosides which have been selectively protected by the process of metal complexation followed by treatment with protecting reagent and subsequent removal of the divalent metal ion contain only two unprotected amino groups. These unprotected amino groups can then be selectively modified. For example, one of the amino groups can be protected using a protecting reagent which is the same as or different from the protecting reagent used in the protection of the other amino groups. This protection is then followed by modification of the remaining unprotected amino group with the moiety of interest, such as a linker, a label, or a carrier. Alternatively, one of the amino groups can be selectively modified with the moiety of interest. This modification is carried out by reacting the unprotected amino group with a reactive substance containing the moiety of interest.

The moiety of interest and the reagent(s) used to link the moiety to the aminoglycoside are dependent on the desired use of the final derivatized aminoglycoside. For example, the moiety of interest may be a fluorescent label moiety which can exhibit different polarization behaviors depending on the environment of the aminoglycoside. The fluorescent moiety may be bonded to the aminoglycoside by a linking group or it may be bonded directly to the aminoglycoside. In general, a label or carrier is defined as including any chemical species which attaches it to the aminoglycoside. For example, a ploy (amino acid) carrier includes any chemical species between the poly)amino acid) and the aminoglycoside, whether or not the chemical species contains amino acids.

In another example, the moiety of interest may be a linker containing an activating group which may undergo a chemical reaction after the linker has been bonded to the aminoglycoside. This activating group can then undergo a further reaction to link the aminoglycoside to another substance. Examples of activating groups include active esters, isocyanates, isothiocyanates, thiols, imidazolyl groups, maleimides, carboxylic acids, and biotin. This approach is typically used for linking aminoglycosides to high molecular weight substances such as natural polymers, synthetic polymers, and poly(amino acids).

Figure 19:
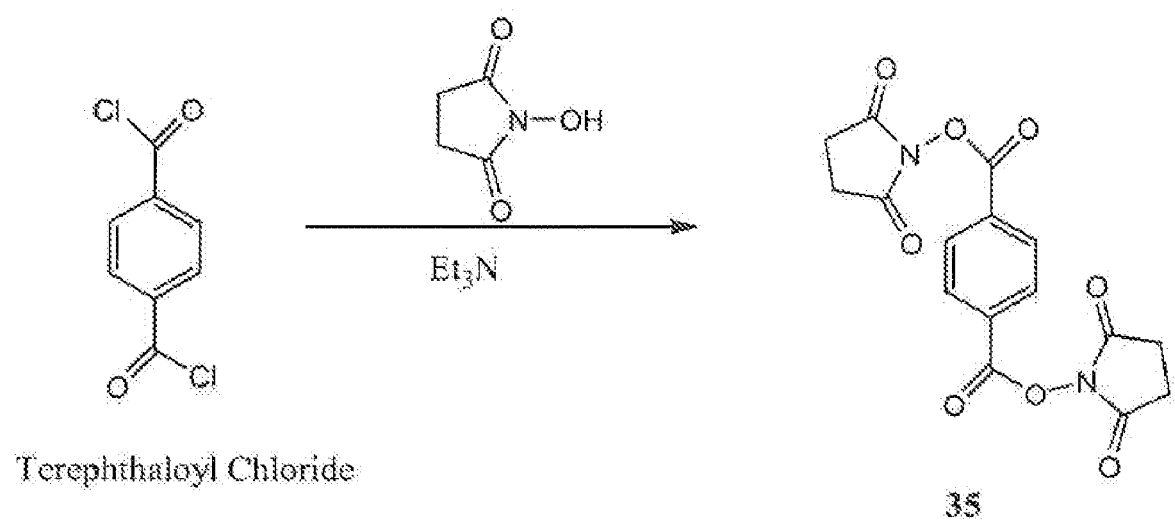
FIG. 19 is a reaction scheme for the synthesis of 1,4-di-N-hydroxysuccinimide ester of terephthalic acid.
Figure 20:
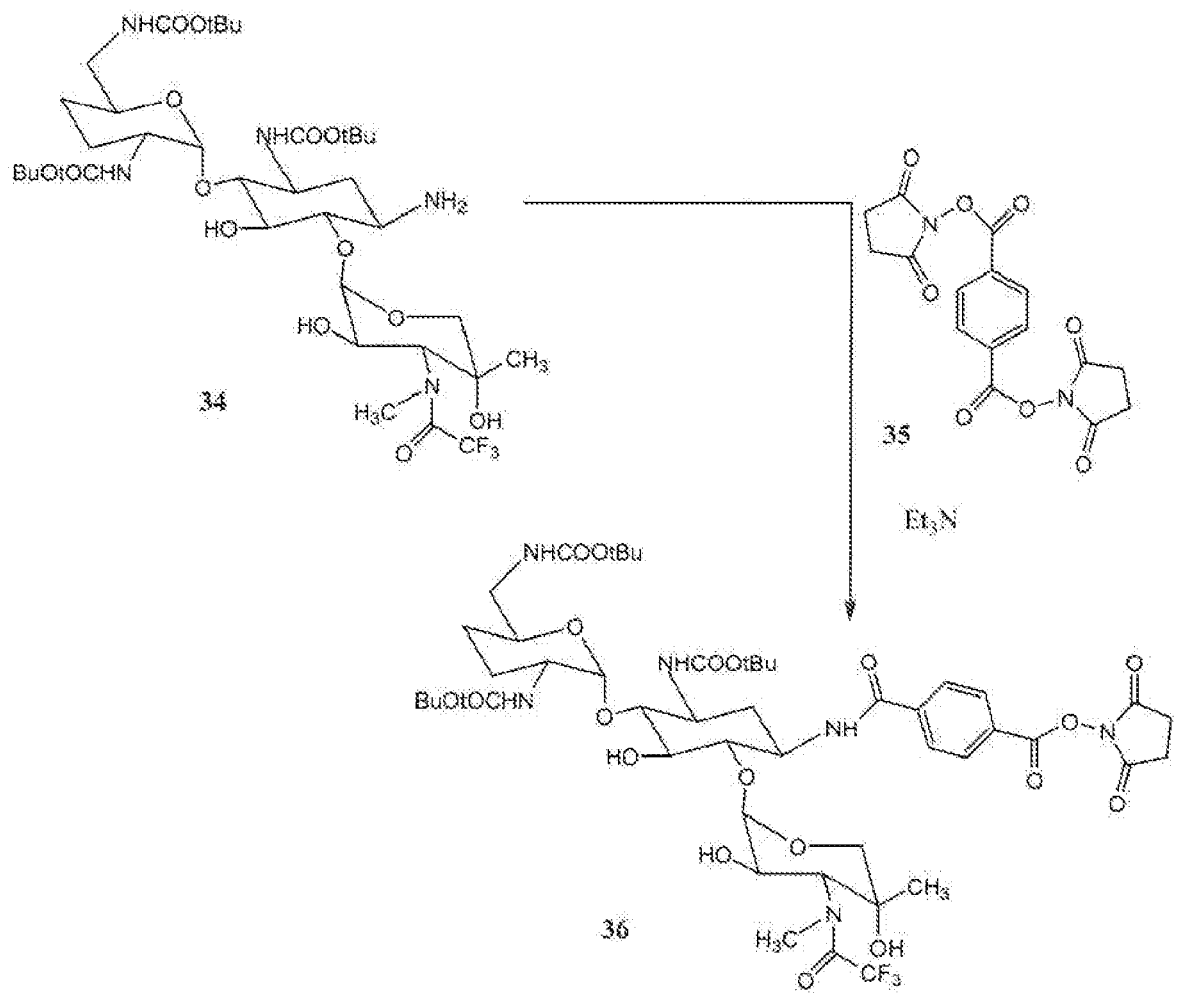
FIGS. 20 and 21 are reaction schemes for the conjugation of gentamicin to aminodextran.
Figure 21:
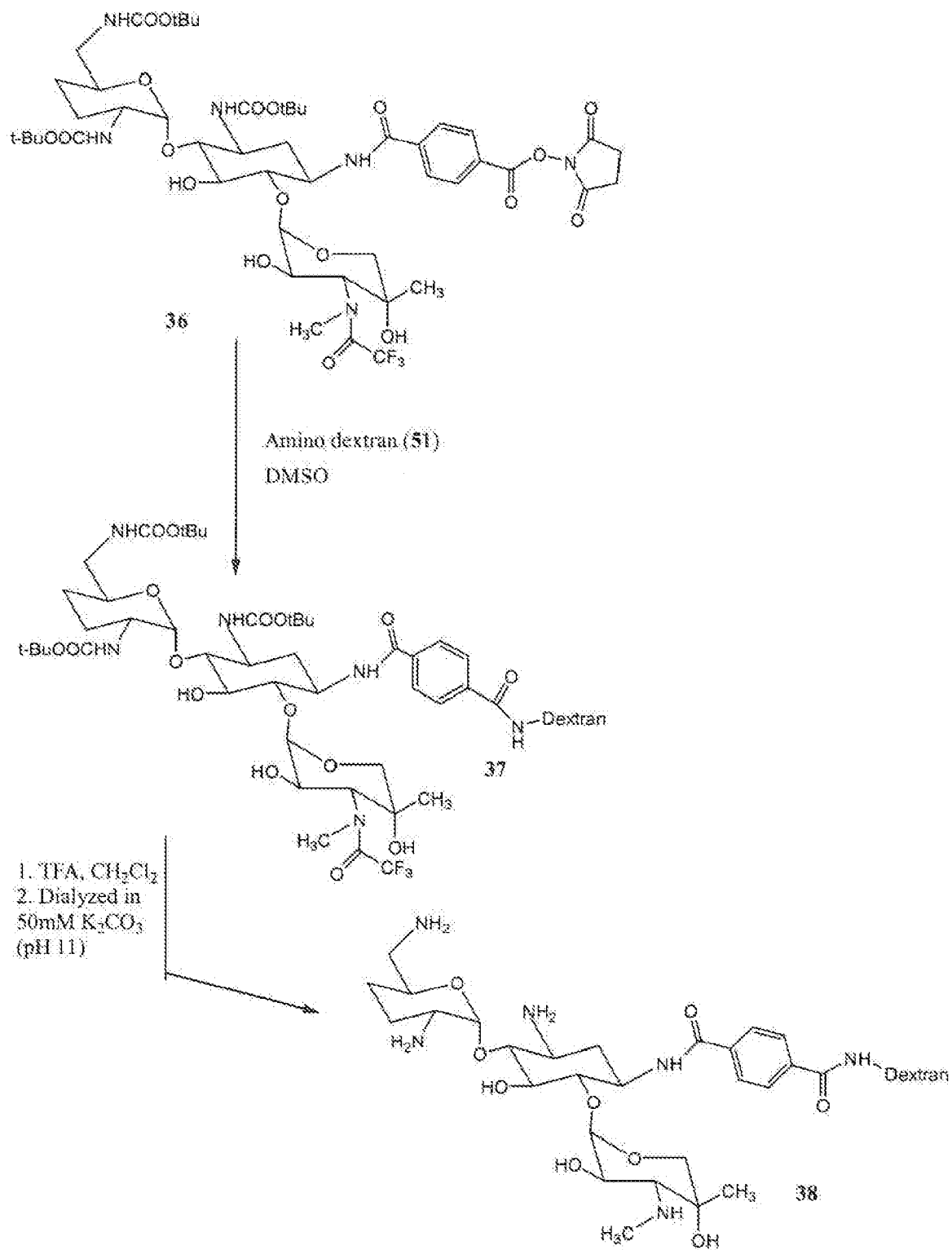
Figure 23:
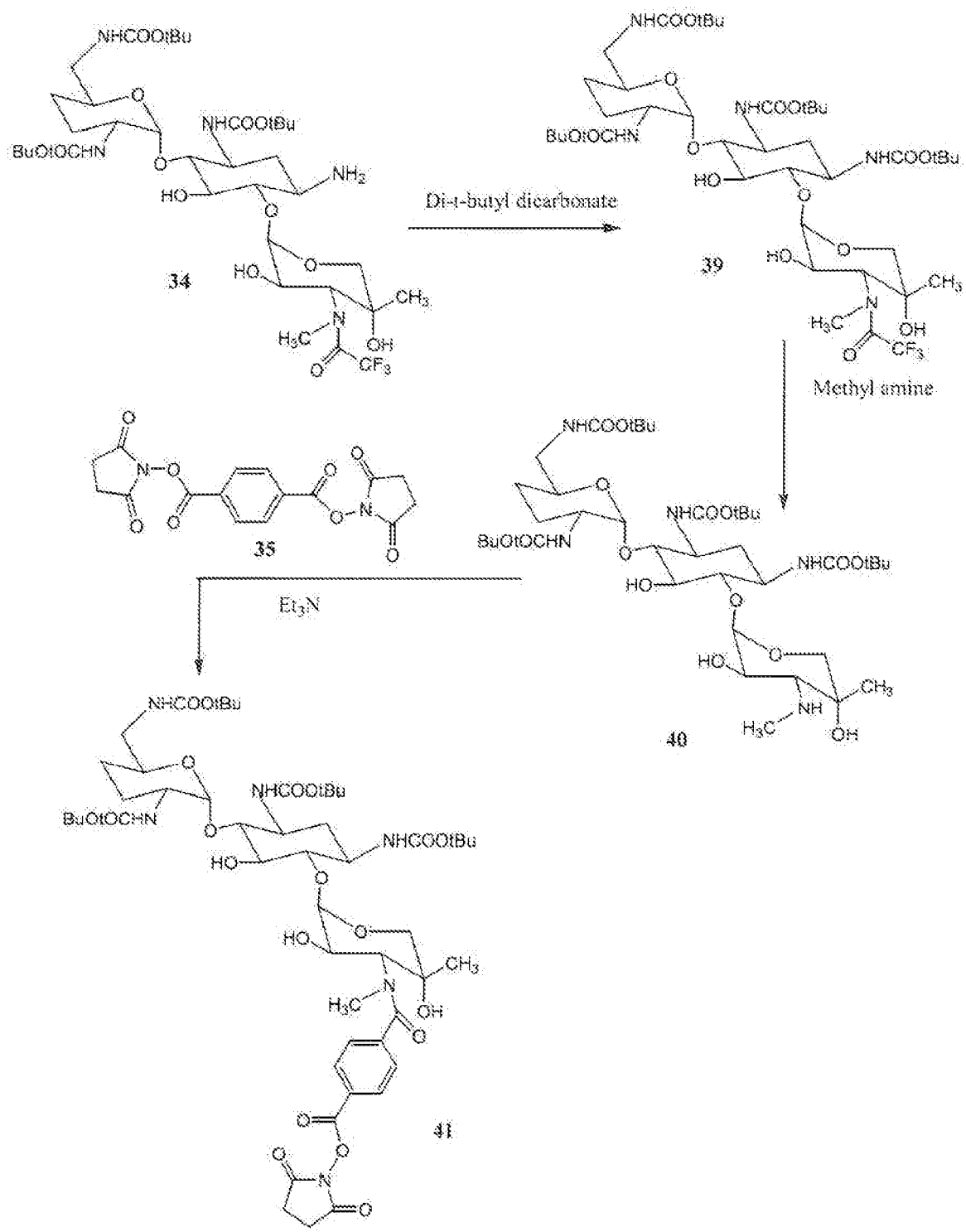
FIG. 23 is a reaction scheme for the synthesis of a gentamicin derivative which can be conjugated.

For example, the reagent used to link the moiety to the aminoglycoside may contain two reactive groups such as the two N-hydroxysuccinimide groups in compound 35 (FIG. 19). In this example, one of the reactive groups reacts with an amino group on the aminoglycoside while the other reactive group functions as the activating group for coupling the aminoglycoside to another substance. Examples of this strategy are illustrated in FIGS. 20-21 and 23, where the N-hydroxysuccinimide activating group on the linker can be used to form conjugates of the aminoglycoside with a label, such as a fluorescent moiety or a polymer, or with a carrier, such as a poly(amino acid) or a polysaccharide.

Figure 29:
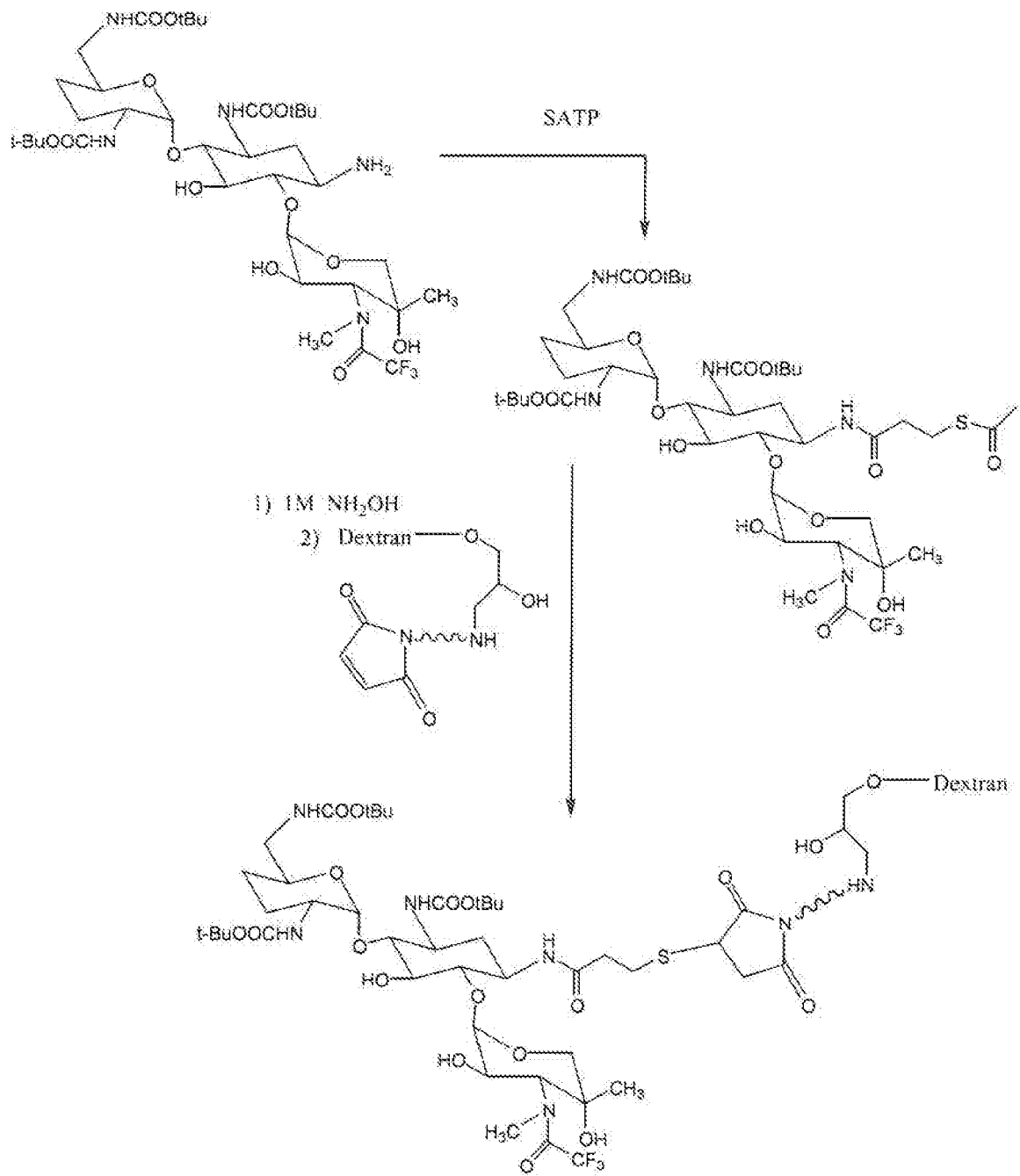
FIG. 29 is a reaction scheme for the conjugation of a gentamicin derivative to aminodextran.

Alternatively, the two reactive groups may be different from each other. Examples of these heterofunctional reagents are those which react to form an amide bond with the aminoglycoside at one end and retain a free protected thiol at the other end as the activating group. Some examples of thiolating reagents of this type include 2-iminothiolane (2-IT), succinimidyl acetylthiopropionate (SATP), and succinimido 2-pyridyldithiopropionate (SPDP). the activating group is then available to form thioethers with carriers or labels modified with maleimide or bromoacetyl groups. The thioether Hformation may be carried out as described in U.S. Pat. No. 5,976,812 (Example 3) with the use of hydroxylamine (NH$_2$OH) followed by treatment with the modified carrier or label. An example of this strategy is illustrated in FIG. 29.

Figure 30:
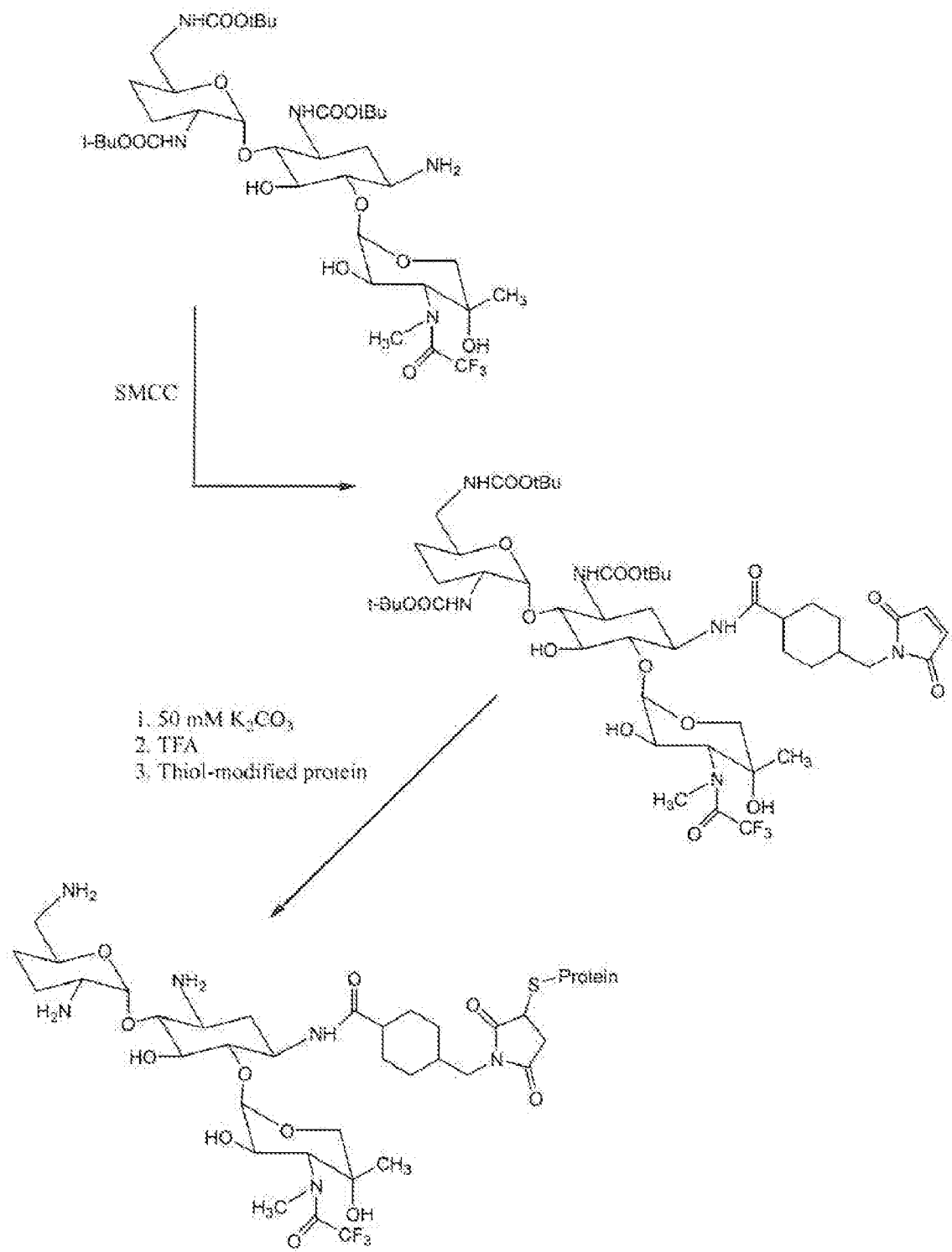
FIG. 30 is a reaction scheme for the synthesis of a gentamicin immunogen.

Further examples of activating groups include maleimide groups, which can form conjugates with carriers modified with thiol groups (FIG. 30); biotin, which can form conjugates with avidin/streptavidin; and carboxylic acid groups (FIGS. 10, 17, 25, and 27). Yet another example includes urea and thiourea groups, which may be formed by the reaction of an amino group on the aminoglycoside with a reagent such as 4-nitrochloroformate, phosgene, thiophosgene, or similar reagents such as carbonyldiimidazole or disuccinimidyl carbonate.

The linking group, whether containing an activating group or acting as a linker between the aminoglycoside and a label or a carrier, may be any carbon chain. Preferably, the linking group is a moiety containing from 1 to 20 carbon atoms and can be straight or branched. The chain and any branches may independently contain multiple carbon-carbon bonds, heteroatoms, and aromatic or non-aromatic rings. More preferably, the linking group contains from 1 to 10 carbon atoms.

Following the modification with the moiety of interest, deprotection of the amino groups which have been modified with protecting groups yields the final product of a site-specific aminoglycoside derivative. This product is then isolated from the reaction mixture, for example, by preparative then layer chromatography, by silica gel chromatography, or by dialysis.

Because each step of the process produces a site-specific intermediate, the final isolated product does not contain significant amounts of aminoglycoside which have been modified at different places on the molecule or which have been unmodified or modified more than once (non-site-specific). Preferably, the isolated product contains no more than 10% of non-site-specific derivatives. More preferably, the isolated product contains no more than 5% of non-site-specific derivatives. Even more preferably, the isolated product contains no more than 3% of non-site-specific derivatives. Even more preferably, the isolated product contains no more than 1% of non-site-specific derivatives. These values correspond to product purities of 90%, 95%, 97%, and 99% respectively. The term "product purity" means the percentage of derivatized aminoglycosides in the isolated product which are site-specific, as measured by high performance liquid chromatography (HPLC). The isolated aminoglycoside derivatives (analyte analogs) can then be used as reagents in assays for the underivatized aminoglycosides (analytes).

Examples of site-specific aminoglycoside derivatives suitable for use in fluorescence polarization (FP) assays are illustrated in FIGS. 6-8 and 14. Any aminoglycoside may be modified with a fluorescein moiety for use as an FP tracer.

Fluorescence polarization is well known in the immunoassay field as providing a quantitative means for measuring the amount of tracer-antibody conjugate produced in a competitive binding immunoassay (see *Biochem. Biophys. Res. Comm.* 5:299, 1961, which is incorporated herein by reference). In general, fluorescent polarization techniques are based on the principle that a fluorescein labeled compound, when excited by linearly polarized light, will emit fluorescence having a degree of polarization inversely related to its rate of rotation. Several fluorescein derivatives from which fluorescein labeled tracers can be prepared are known and are commercially available. The majority of fluorescein derivatives are derived from the 5- or 6-position of fluorescein (also referred to as isomer I for the 5-position and isomer II for the 6-position) and include 5- or 6-N-hydroxysuccinimidylcarboxyfluorescein, 5-aminomethylfluorescein and 5- or 6-dichloro-1,3,5-triazin-2-ylaminofluorescein (DTAF).

In FP immunoassay, fluorescence polarization is a reproducible function of the ligand or drug concentration and thus is suitable for the quantitative determination of ligand or drug (analyte) concentrations in serum for the purpose of therapeutic drug monitoring. When tracer, serum containing antibodies specific for the analyte to be measured, and analyte-free patient serum are mixed together, most of the tracer binds to the antibodies. As a result, when the bound tracer is excited with polarized light at 489 nm, the light emitted at 520 nm remains highly polarized. However, if analyte is present in the patient sample, the analyte will compete with the tracer for binding to the antibodies. Thus, more of the tracer will remain unbound and the emitted light is depolarized.

The results of FP immunoassays can be quantified in terms of millipolarization units (mP), from which a calibration curve can be determined and the span can be calculated. The span is the difference (or delta) between the maximum and minimum binding as measured in mP units (delta mP) of the tracer to the antibody as the free analyte competes with the bound tracer for antibody binding sites. A larger span provides for better precision. The polarization of fluorescence decreases in a regular manner as the concentration of the analyte increases. The higher the delta value, or span, the better the precision and sensitivity of the assay. The concentration of analyte in the sample can be determined by comparison to a standard calibration curve. Fluorescence polarization assays, including procedures, instrumentation, and reagents, are described in U.S. Pat. Nos. 5,986,094 and 4,868,132 and in European Patent Application EP 0 745 602 A1, which are incorporated herein by reference.

Examples of site-specific aminoglycoside derivatives suitable for use in kinetic interaction of microparticles in solution (KIMS) assays are illustrated in FIGS. 10, 17, 21, and 25. Any aminoglycoside may be modified with a poly(amino acid) or polymer moiety for use as a conjugate in KIMS.

The KIMS assay is based on the kinetic interaction of microparticles in solution as measured by changes in light transmission. In the absence of analyte, analyte analog conjugates can bind to antibody-bound microparticles, resulting in the formation of particle aggregates. As the aggregation proceeds (in the absence of analyte), the absorbance of the mixture increases. When a biological sample containing the analyte is present, the analyte competes with the conjugate-bound analyte analog for binding to the microparticle-bound antibody. Antibody that is bound to the analyte (and not to the conjugate-bound analyte analog) is no longer available to participate in particle aggregation. The presence of analyte thus diminishes the increase in absorbance, and this effect is in proportion to the concentration of analyte in the sample. Analyte content is determined relative to the values obtained for known concentrations of the analyte (Adler, F. L. *J. Immunol.* 106(6):1684-1685, 1971. See also Bates, M. *Amer. Acad. Forensic Sci.* 37(6): 1000, 1991).

Immunogens made according the present invention may be used to generate antibodies. The immunogen may be prepared for injection into a host animal by rehydrating lyophilized immunogen to form a solution or suspension of the immunogen. The immunogen solution is then combined with an adjuvant such as Freund's, and may be administered in a variety of sites using several doses. Preparation of polyclonal antibodies using the immunogen may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesirable material such as nonspecific antibodies before the antiserum is considered suitable for use in the performing assays. Monoclonal antibodies may be obtained by hybridizing mouse lymphocytes, immunized as described above, and myeloma cells using a polyethylene glycol method such as the technique described in *Methods in Enzymology* 73 (Part B), pp 3-46, 1981. Conjugates with bovine serum albumin (BSA) are preferred for coating of microtiter plates for use in ELISA. This method has been used to screen the antibodies and is well-known to those skilled in the art.

Various ancillary material will frequently be employed in an assay in accordance with the present invention. For example, buffers will normally be present in the assay medium, as well as stabilizers for the assay medium and the assay components. Frequently, in addition to these additives, additional proteins may be included such as albumin or surfactants, particularly non-ionic surfactants and the like.

The aminoglycoside derivatives may, along with other regents, be packaged in a kit useful for conveniently performing the assay methods for the determination of an analyte. To enhance the versatility of the subject invention, reagents can be provided in packaged combination, in the same or separate containers, in liquid or lyophilized form so that the ratio of the reagents provides for substantial optimization of the method assay. The reagents may each be in separate containers, or various reagents can be combined in one or more containers depending on the cross-reactivity and stability of the reagents.

For example, a reagent test kit may contain, in packaged combination, an antibody specific for a particular aminoglycoside, a complex comprising a ligand of an aminoglycoside derivative coupled to a labeling moiety, and optionally one or more calibrators comprising a known amount of an aminoglycoside. Such a test kit may provide reagents for an assay with enhanced clinical sensitivity for aminoglycosides and structurally related compounds.

EXAMPLES

The following examples are provided by way of illustration and should not be seen as limiting the scope of the present invention.

Tobramycin, kanamycin sulfate, and gentamicin sulfate were purchased from Fluka (Milwaukee, Wis.) Gentamicin sulfate was converted to free base using AMBERLITE IRA-410 ion exchange resin (strongly basic), and the resulting gentamicin C complex was separated by following the literature procedure to separate gentamicin $C_1$, $C_{1a}$ and $C_2$, (David J. Cooper, J. *Chem Soc.*, 2876-2879, 1971). Solvents were obtained from Fisher Scientific (Suwanee, Ga.). All other reagents were obtained from Aldrich (Milwaukee, Wis.) or from Fluka and were used as received.

Example 1

Figure 4:
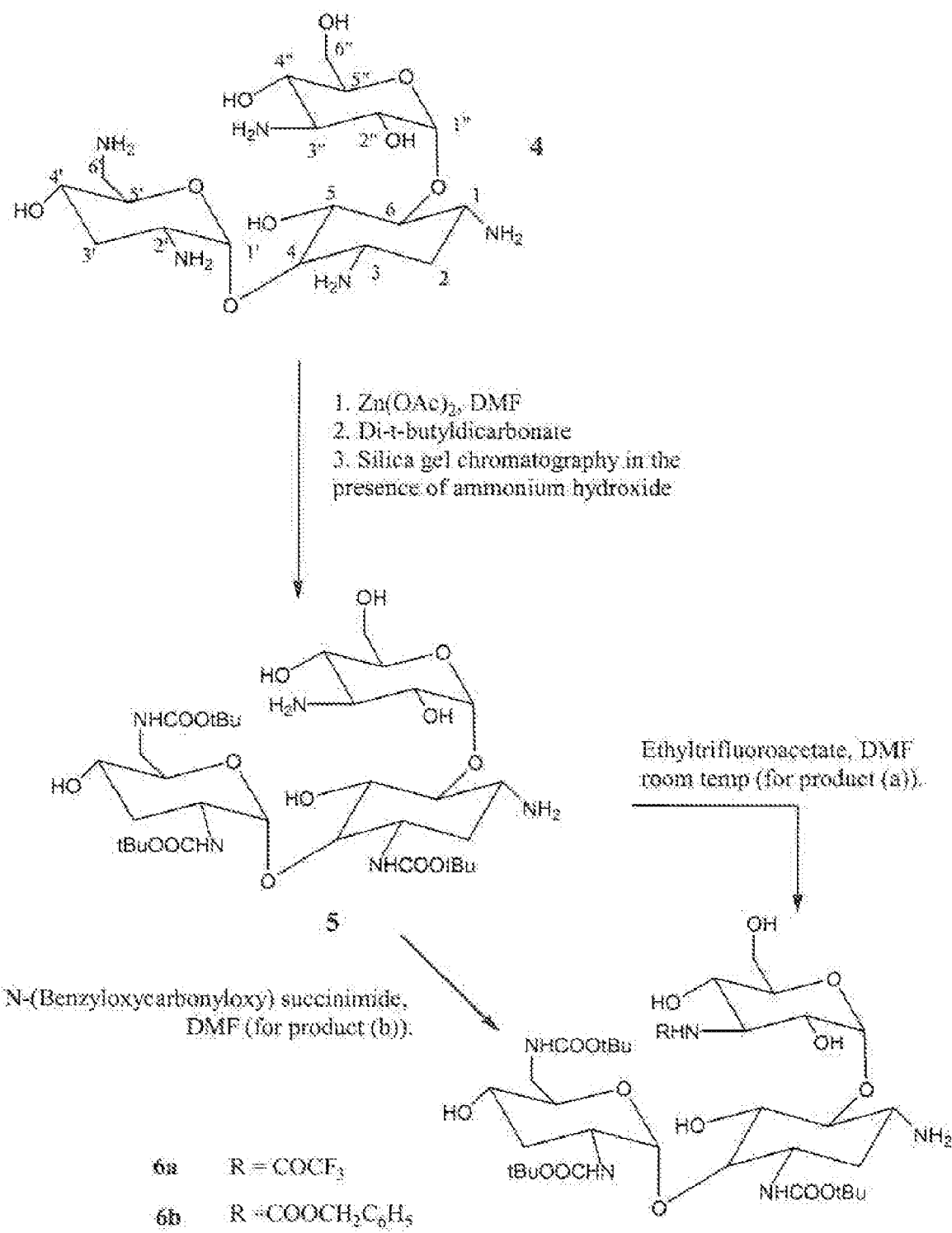
FIGS. 4 and 5 are reaction schemes for the selective protection of tobramycin.
Figure 5:
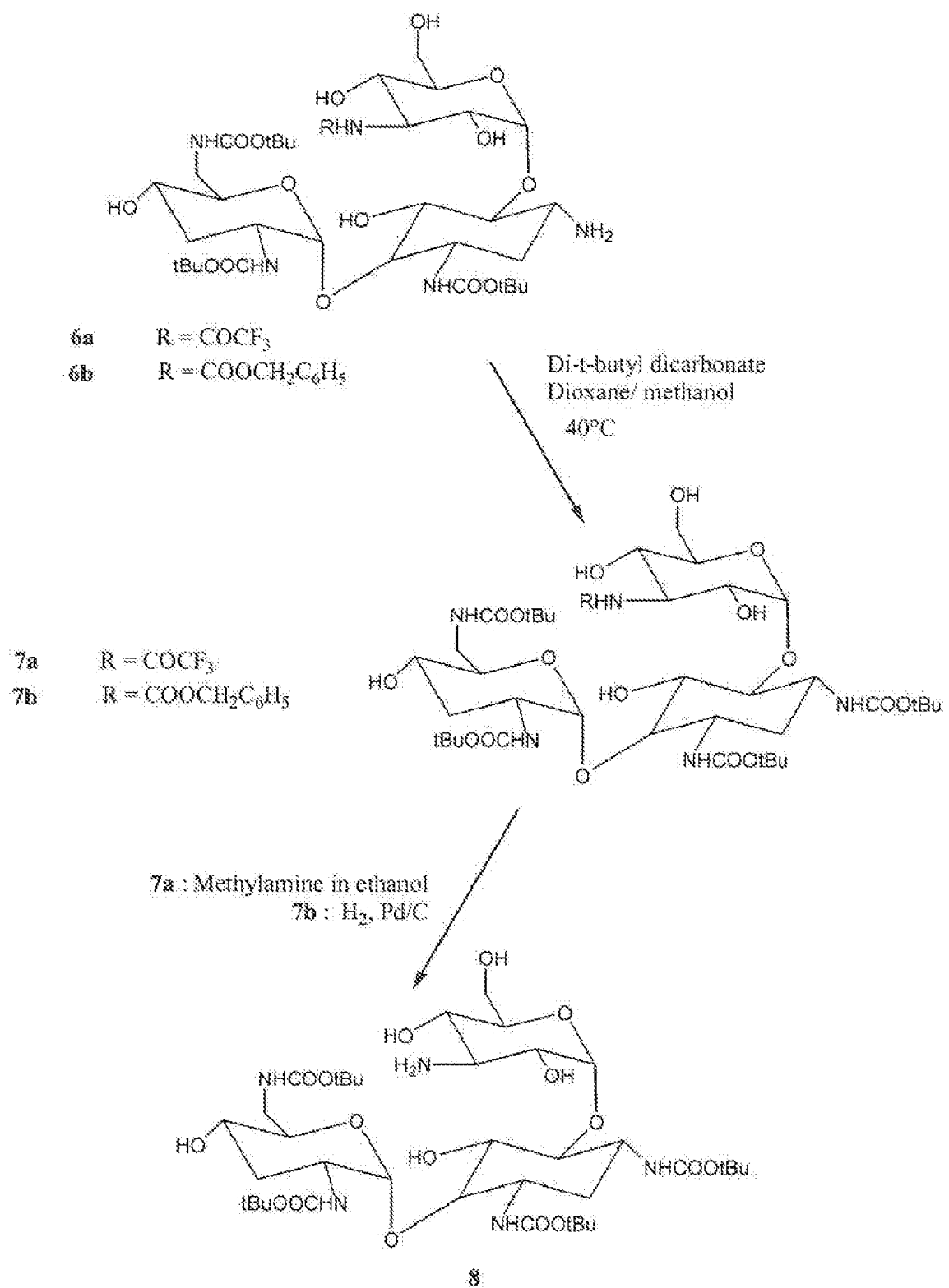

Synthesis of Protected Tobramycin (FIGS. 4-5)

Synthesis of 3,2',6'-tris-N-(tert-butoxycarbonyl)tobramycin (5). To a suspension of 3 g (6.41 mmol) of tobramycin (4) in 180 mL of anyhdrous dimethyl formamide (DMF) was added 5.76 g (26.2 mmol) of zinc acetate dihydrate. The mixture was allowed to stir at room temperature under argon atmosphere for 3 days. To the reaction mixture was added 4.59 g (21 mmol) of di-t-butyldicarbonate, and the reaction mixture was allowed to stir for 3 days and then concentrated. The residue was purified by silica gel column chromatography using chloroform (CHCl$_3$)-methanol (MeOH)-28% ammonium hydroxide (NH$_4$OH) (7:30.75) as eluent to give 2.5 g (3.25 mmol, 51%) of 5 as a white solid.

3,2',6'-Tris-N-(tert-butoxycarbonyl)-3"-N-trifluoroacetyl) tobramycin (6a). To a solution of 320 mg (0.42 mmol) of 5 in 2 mL of anhydrous dimethylsulfoxide (DMSO) was added 54 µL (0.45 mmol) of ethyl trifluoroacetate. The mixture was allowed to stir at room temperature for 3 hours and then concentrated. The residue was purified by silica gel column chromatography using 60% CHCl$_3$ in methanol to give 331 mg (0.38 mmol, 92%) of 6a as a colorless thick oil.

3,2',6'-Tris-N-(tert-butoxycarbonyl)-3"-N-(benzyloxycarbonyloxy) tobramycin (6a). To 145 mg (0.19 mmol) of 5 was added 3 mL of anhydrous DMF followed by 47 mg (0.19 mmol) of N-benzyloxycarbonyloxy) succinimide. The mixture was allowed to stir for 48 hours at room temperature and then concentrated under reduced pressure. The residue was purified by silica gel column chromatography using an 8:2 mixture of CHCl$_3$ and MeOH to give 150 mg (0.17 mmol, 88%) of 6b as a white powder.

1,3,2',6'-Tetrakis-N-(tert-butoxycarbonyl)-3"-N-(trifluoroacetyl) tobramycin (7a). to 90 mg (0.104 mmol) of 6a was added 4.8 mL of a 20:1 mixture of dioxane and methanol followed by 220 mg (1.0 mmol) of di-t-butyldicarbonate. The mixture was allowed to stir at room temperature 30 minutes and at 40-50° C. for 30 minutes. This mixture was then concentrated and purified by column chromatography to give crude product containing impurities. To the crude product was added 7 mL of methanol and 600 µL of 28% NH$_4$OH. The resulting mixture was concentrated and then treated with 25 mL of diethyl ether. The resulting white precipitate was filtered to give 55 mg (0.057 mmol, 55%) of 7a.

1,3,2',6'-Tetrakis-N-(tert-butoxycarbonyl)-3"-N-(benzyloxy-carbonyloxy) tobramycin (7b). To 25 mg (0.027 mmol) of 6b was added 1.2 mL of a 20:1 mixture of dioxane and methanol followed by 60 mg (0.27 mmol) of di-t-butyl-dicarbonate. The mixture was allowed to stir at room temperature for 0.5 hour and then at 40° C. to 50° C. for 0.5 hour. To the reaction mixture was added 142 µL of concentrated NH$_4$OH. The resulting mixture was concentrated by rotary evaporation and treated with 10 mL of diethyl ether, and the solid formed was collected to give 27 mg (0.26 mmol, 97%) of 7b as a white solid.

1,3,2',6'-Tetrakis-N-(tert-butoxycarbonyl)-tobramycin (8). To 40 mg (0.041 mmol) of 7a or 7b was added 2 mL of methanol and 800 µL of a 4 M solution of methyl amine in ethanol. The mixture was allowed to stir at room temperature for 30 minutes and then at 75° C. for 2.5 hours. The reaction mixture was concentrated and then with 5 mL of dry dichloromethane. The resulting mixture was concentrated to give 34 mg (0.039 mmol, 94%) of 8 as a white powder.

Example 2

Figure 6:
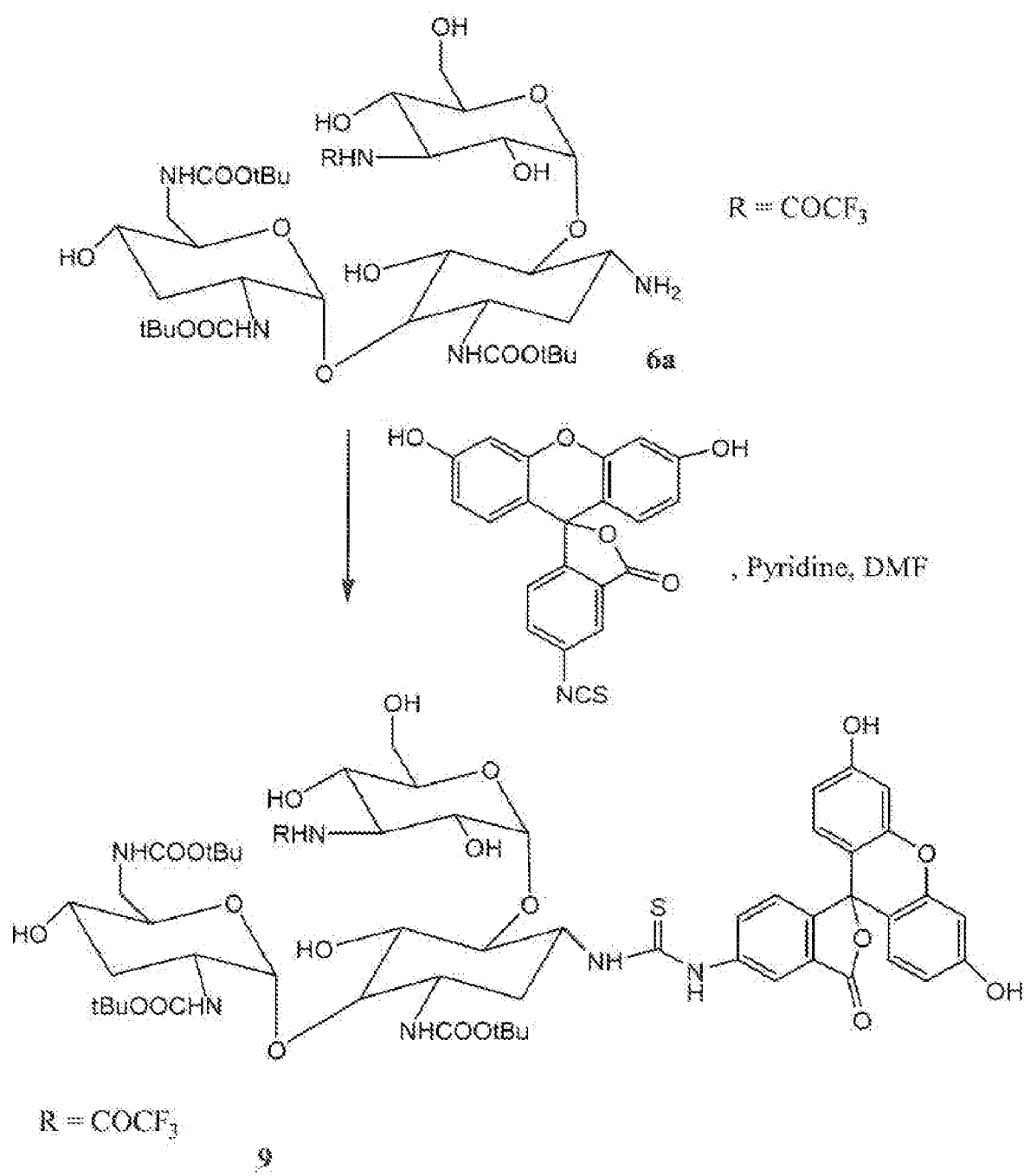
FIGS. 6-8 are reaction schemes for the syntheses of FP tracers of tobramycin.
Figure 7:
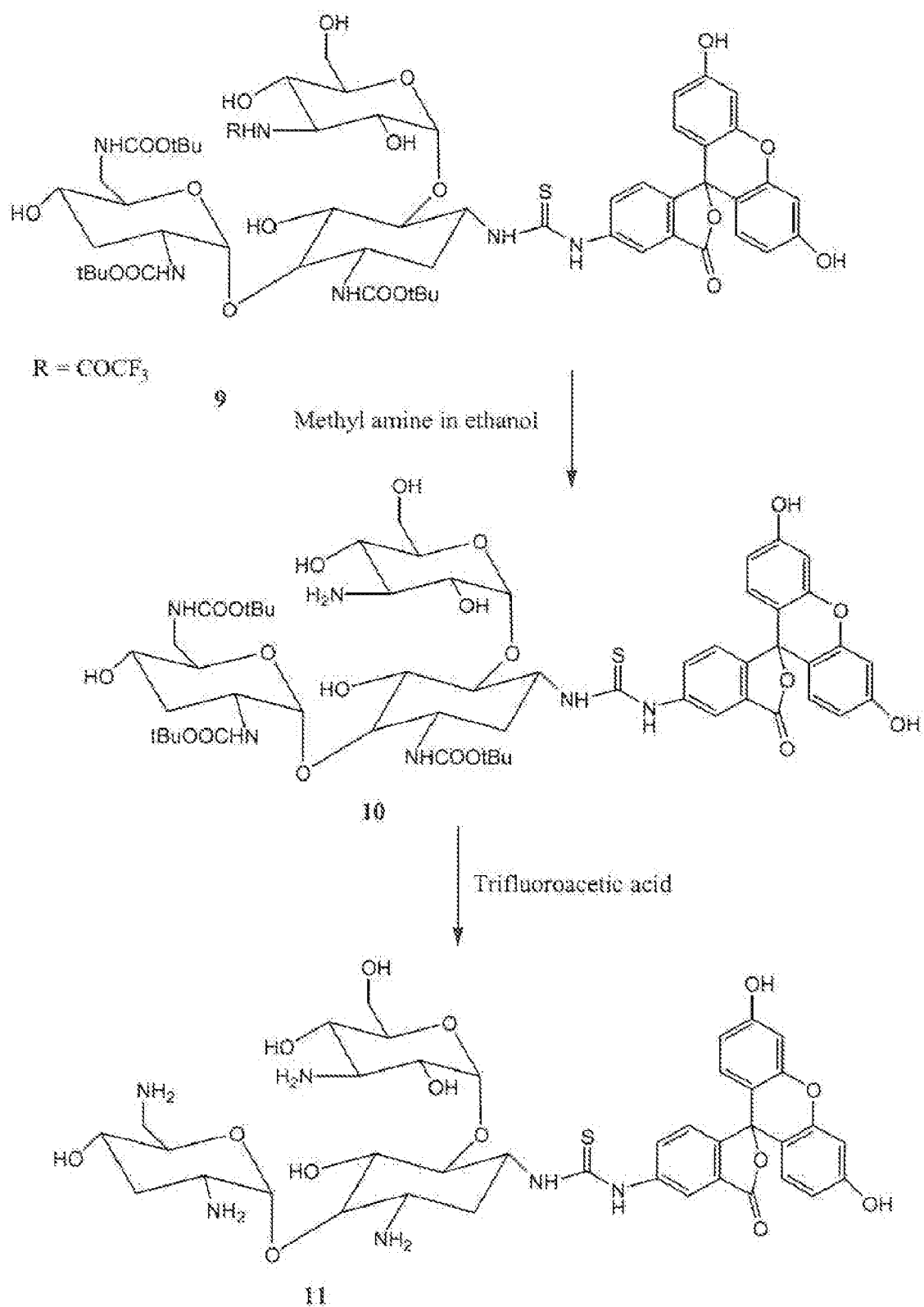

Synthesis of Tobramycin FP Tracer (FIGS. 6-7)

3,2',6'-Tris-N-(tert-butoxycarbonyl)-N-3"(trifluoroacetyl) 1-tobramycin 1-N-position fluorescein substituted conjugate (9). To 50 mg (0.057 mmol) of 6a was added 1.5 mL anhydrous pyridine and 1.5 mL of anhydrous DMF. To the reaction mixture was added 38 mg (0.097 mmol) of fluorescein isothiocyanate (isomer 1). The reaction mixture was allowed to stir at room temperature 18 hours and was then concentrated. The residue was purified by preparative thin layer chromatography using 15% methanol in chloroform to give 32 mg (0.025 mmol, 44%) of 9 as an orange powder.

3,2',6'-Tris-N-(tert-butoxycarbonyl)-tobramycin 1-N-position fluorescein substituted conjugate (10). To 30 mg (0.023 mmol) of 9 was added 1 mL of a 4 M solution of methylamine in ethanol. The mixture was heated to 60° C. for 2.5 hours and concentrated. To the residue was added 5 mL of methanol and concentrated. The addition of methanol and concentration procedure was repeated twice to give 25 mg (0.021 mmol, 92%) of 10 as an orange-red powder.

Tobramycin 1-N-position fluorescein substituted conjugate (11). To 37 mg (0.031 mmol) of 10 was added 3 mL of trifluoracetic acid. The mixture was allowed to stir at room temperature for 15 minutes and was than concentrated. The residue was purified by preparative thin layer chromatography using methanol-28% NH$_4$OH-water to give 18 mg (0.021 mmol, 66%) of 11 as an orange-red powder.

Example 3

Figure 28:
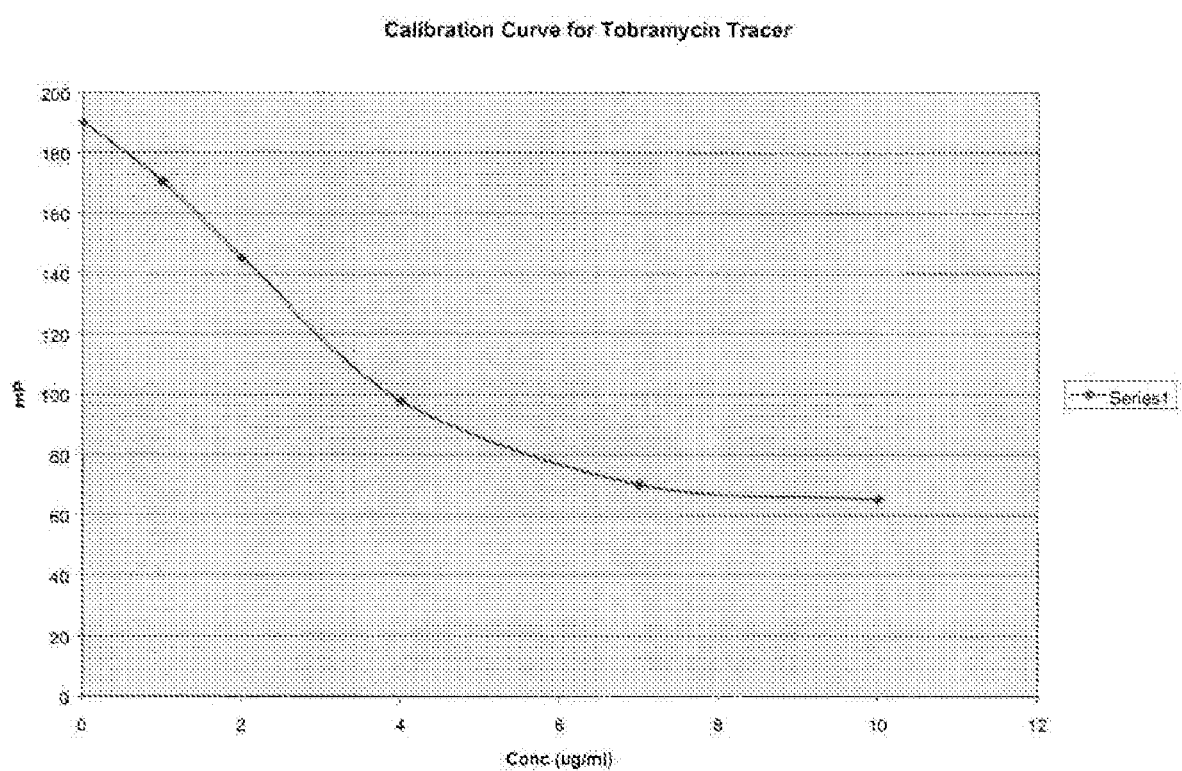
FIG. 28 is a graph showing standard (dose response) curves generated from data using conjugates and antibodies of tobramycin in a fluorescence polarization immunoassay.

Immunoassay Utilizing Tobramycin FP Tracer (FIG. 28)

An immunoassay was performed using a COBAS FARA II analyzer (Roche Diagnostics Corporation, Indianapolis) using assay reagents and protocols in accordance with the operation manual for the instrument. The instrument was configured for fluorescence polarization measurements for tobramycin in serum or plasma sample. The reagent formulations used were the following:

a) Antibody reagents containing anti-tobramycin antiserum in 0.1 M phosphate buffer, pH 7.5, with 0.15 M NaCl, 0.01% bovine serum albumin, and 0.09% sodium azide (COBAS INTEGRA reagents for tobramycin, Order No. 44530)

b) FP tracer 11 in 0.05 M phosphate buffer, pH 7.5, containing 0.01% rabbit gamma globulin, 0.09% NaN$_1$, 0.03% EDTA, pH 8.0, containing 13.8 ng/mL of tobramycin tracer 11 c) Tobramycin calibrator, COBAS-FP Tobramicin Calibrators, Article 07 1775 4US#44531 containing 0, 1, 2, 4, 7, and 10 µg/mL (tobramicin concentration)

The assay was run on the COBAS FARA II instrument by using 200 µL of antibody reagent was 30 µL of the calibrator solution and 2.6 µL of the tracer reagent. After completion of the assay, the COBAS FARA II calculated the millipolarization units (mp) of the tracer, and a standard curve was generated as shown in FIG. 28. The concentration of drug in the sample can then be determined by comparison to a standard calibration curve.

Example 4

Figure 8:
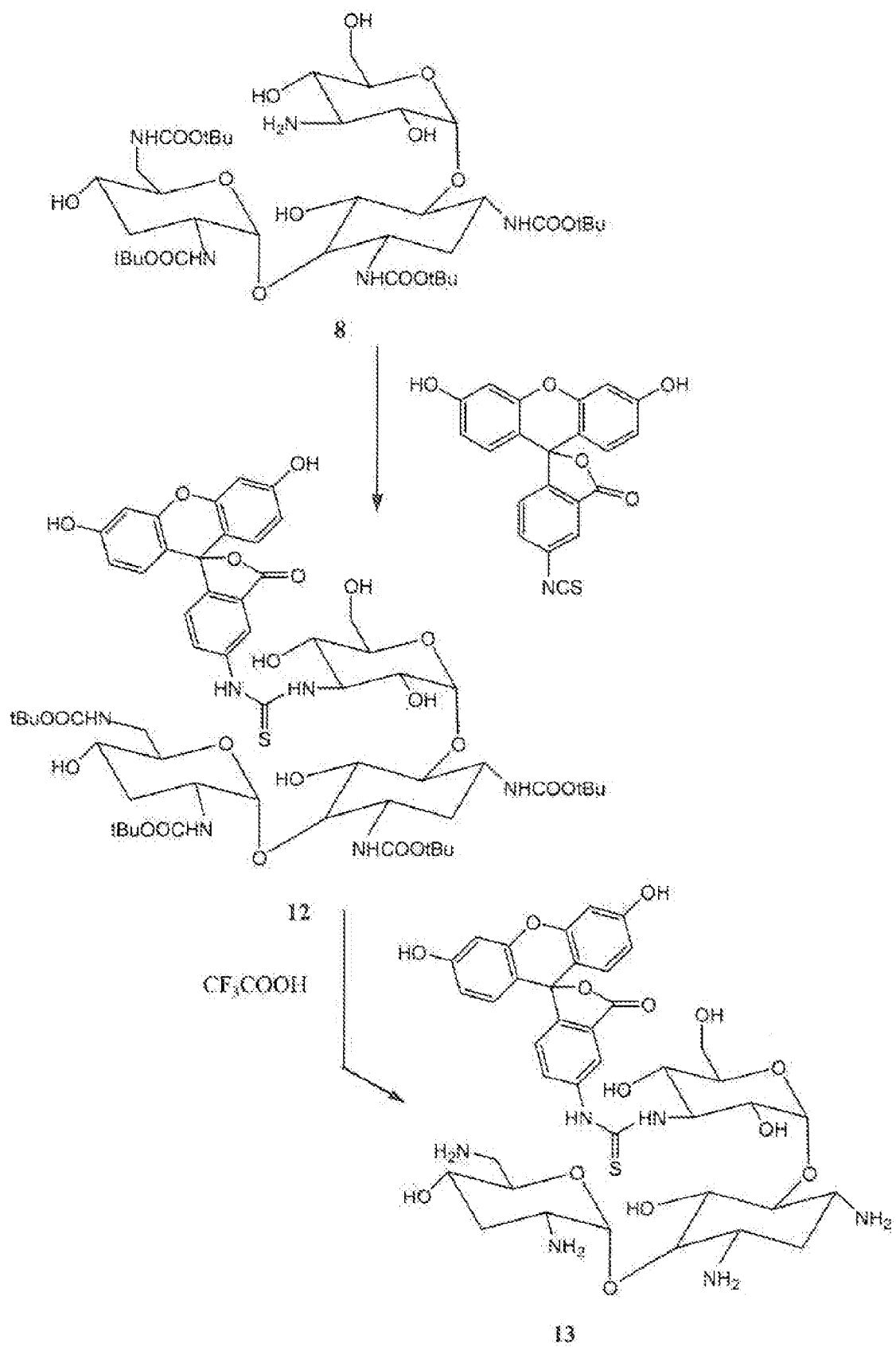

Synthesis of Tobramycin FP Tracer (3"N derivative, FIG. 8)

1,3,2',6'-Tetrakis-N-(tert-butoxycarbonyl)-tobramycin 3"N-fluorescein conjugate (12). To 16 mg (0.018 mmol) of 8 was added 0.5 mL of anhydrous pyridine and 0.5 mL of anhydrous DMF. To this reaction mixture was added 9 mg (0.023 mmol) of fluorescein isothiocyanate (isomer 1). The mixture was allowed to stir at room temperature 18 hours and was then concentrated. The residue was purified by preparative thin layer chromatography using 20% methanol in chloroform to give 12 mg (0.009 mmol, 54%) of 12 as an orange-red powder.

Tobramycin 3"N-fluorescein substituted conjugate (13). To 10 mg (0.008 mmol) of 12 was added 1 mL of trifluoroacetic acid. The mixture was allowed to stir at room temperature for 15 minutes and concentrated. The residue was purified by preparative thin layer chromatography using MeOH: 28% $NH_4OH:H_2O$ (9:0.5:0.5) to give 5.2 mg (0.006 mmol, 86%) of 13 as an orange-yellow powder.

Example 5

Figure 9:
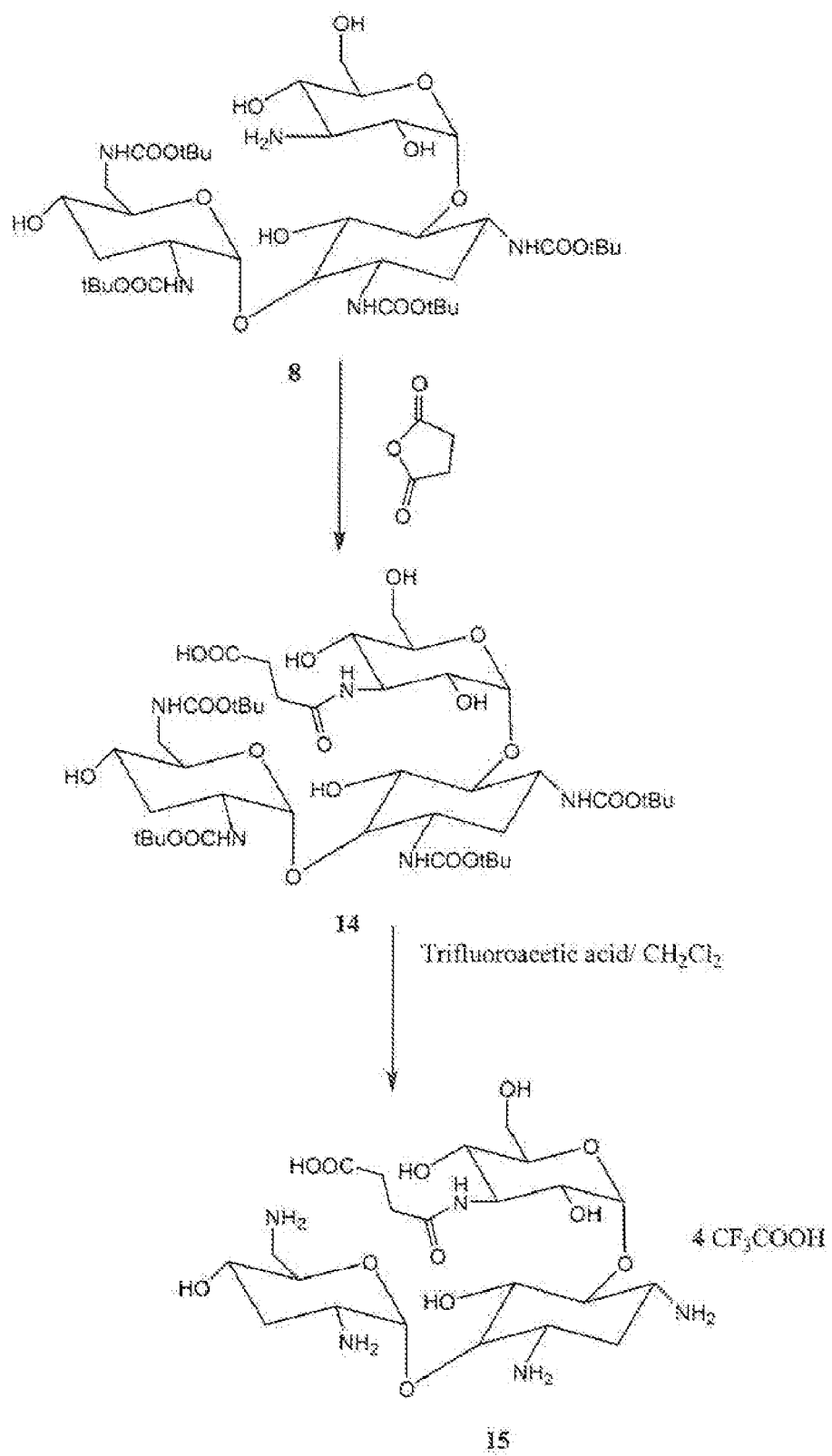
FIGS. 9 and 10 are reaction schemes for the synthesis of tobramycin immunogens.
Figure 10:
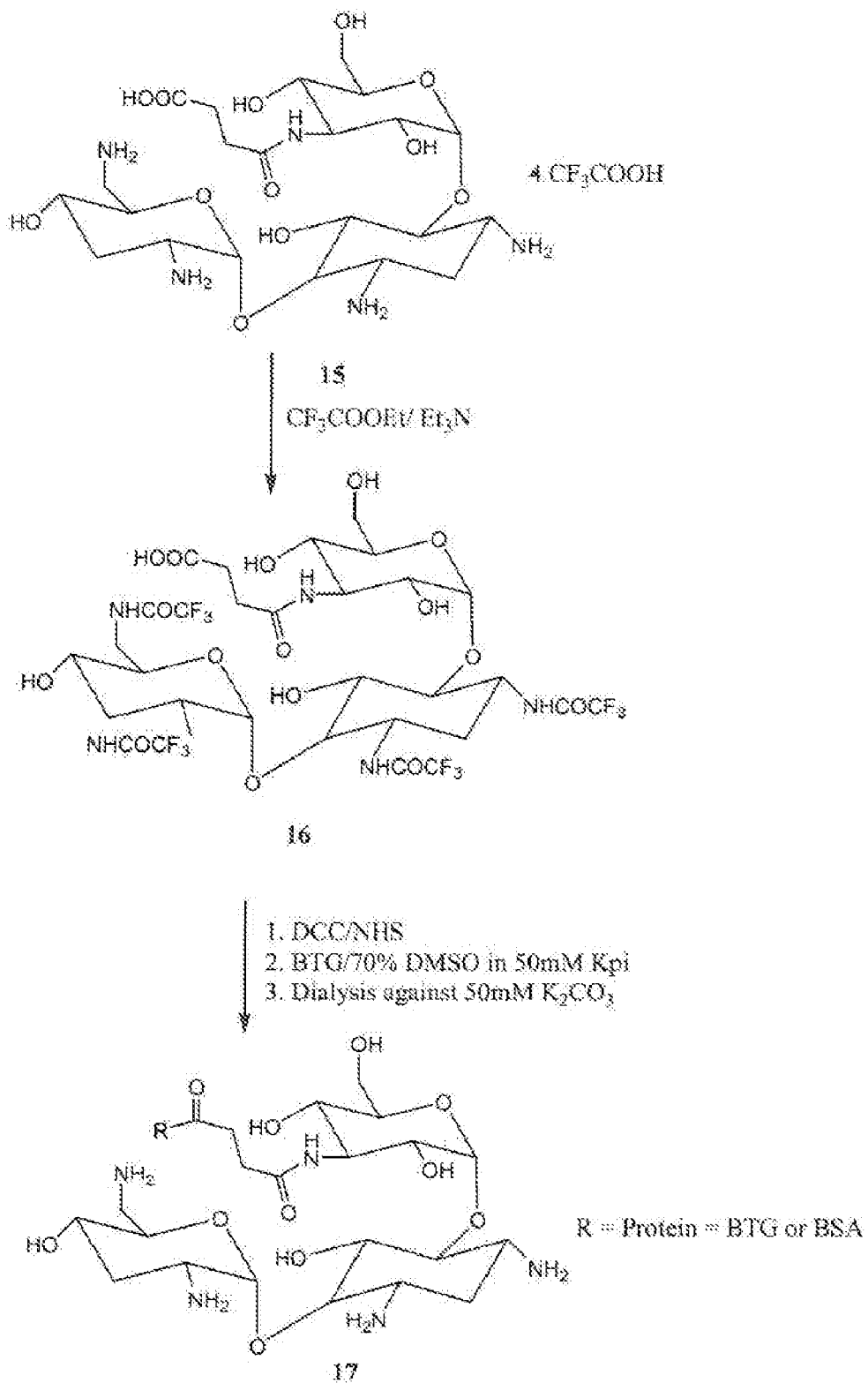

Synthesis of Tobramycin Immunogen (FIGS. 9-10)

1,3,2',6'-Tetrakis-N-(tert-butoxycrabonyl)-Tobramycin-3"N-succinic acid derivative (14). To 100 mg (0.12 mmol) of 8 was added 2 mL of anhydrous DMSO and 14 mg (0.14 mmol) of succinic anhydride. The mixture was allowed to stir at room temperature 18 hours. The reaction was monitored by thin layer chromatography using 20% methanol in chloroform as eluent, which indicated that the reaction was incomplete. To this reaction mixture was added 35 mg (0.34 mmol) of succinic anhydride, and the reaction was allowed to stir at room temperature 72 hours. The reaction mixture was then concentrated and the residue purified by column chromatography using 50% $CHCl_3$ in methanol to give 75 mg (0.77 mmol, 67%) of 14 as a white powder.

Tobramycin-3"N-succinic acid derivative (15). To 50 mg (0.051 mmol) of 14 was added 1 mL trifluoroacetic acid, and the mixture was allowed to stir for 15 minutes. The mixture was concentrated, treated with 10 mL of dichloromethane, and concentrated. The treatment was dichloromethane followed by concentration of the mixture was repeated two more times to give 42 mg (0.041 mmol, 81%) of 15 as a white powder.

1,3,2',6'-Tetrakis-N-(trifluoroacetyl)-tobramycin-3"N-succinic acid derivative (16). To 50 mg (0.048 mmol) of 15 was added 500 µL of anhydrous DMF and 500 µL (3.5 mmol) of triethylamine followed by 157 µL (1.31 mmol) of ethyltrifluoroacetate. The reaction mixture was allowed to stir at room temperature 18 hours and was then concentrated and treated with 0.5 mL of trifluoroacetic acid. The resulting mixture was concentrated, treated with 2 mL of toluene, and concentrated. The treatment with toluene followed by concentration of the mixture was repeated twice to give 45 mg (0.045 mmol, 95%) of 16.

Conjugation to protein with 1,3,2',6'-tetrakis-N-(trifluoroacetyl)-tobramycin 3"N-succinic acid derivative (17). To a solution of 60 mg (0.063 mmol) of the acid 16 in 1.5 mL of anhydrous DMF was added 8.5 mg (0.073 mmol) of N-hydroxysuccinimide and 14.3 mg (0.067 mmol) of dicyclohexylcarbodiimide. The mixture was allowed to stir at 0° C. for 1 hour and stand at 4° C. for 18 hours. The active ester was prepared in situ and then used without isolation.

A solution of 270 mg of bovine thyroglobulin in 4.5 mL of 50 mM potassium phosphate (pH 7.5) was cooled in an ice-bath. To the solution was added dropwise 15 mL of dimethylsulfoxide, and the reaction temperature was maintained below room temperature. To this protein solution, the previously prepared N-hydroxysuccinimide ester ("active ester") solution was added dropwise, and the reaction was slowly stirred at room temperature for 18 hours. The resulting conjugate was placed in a dialysis tube (50,000 MW cut-off) and dialyzed, in order, against 2 L of the following mixtures: 70% DMSO in 50 mM potassium phosphate (Kpi, pH 7.5, room temperature; mixture changed 3 times for treatments of at least 3 hours each), 50% DMSO in 50 mM Kpi (pH 7.5, room temperature, at least 3 hours), 30% DMSO in 50 mM Kpi (pH 7.5, room temperature, at least 3 hours), 10% DMSO in 50 mM Kpi (pH 7.5, room temperature, at least 3 hours), and 50 mM Kpi (pH 7.5, 4° C., mixture changed 4 times for treatments of at least 6 hours each).

The trifluoroacelamido groups of tobramycin were deprotected by dialysis against 50 mM $K_2CO_3$ (pH 11) for 5 days (5 changes, 2 L each day) at room temperature. This was followed by dialysis against 50 mM Kpi (pH 7.5, 4° C.) with 6 changes for 6 hours, 2 L each. The protein concentration was determined by Biorad Coomassie Blue protein assay performed by a modified Bradford method (Bradford, M., *Anal. Biochem.* 72, 248, 1976).

Example 6

Figure 11:
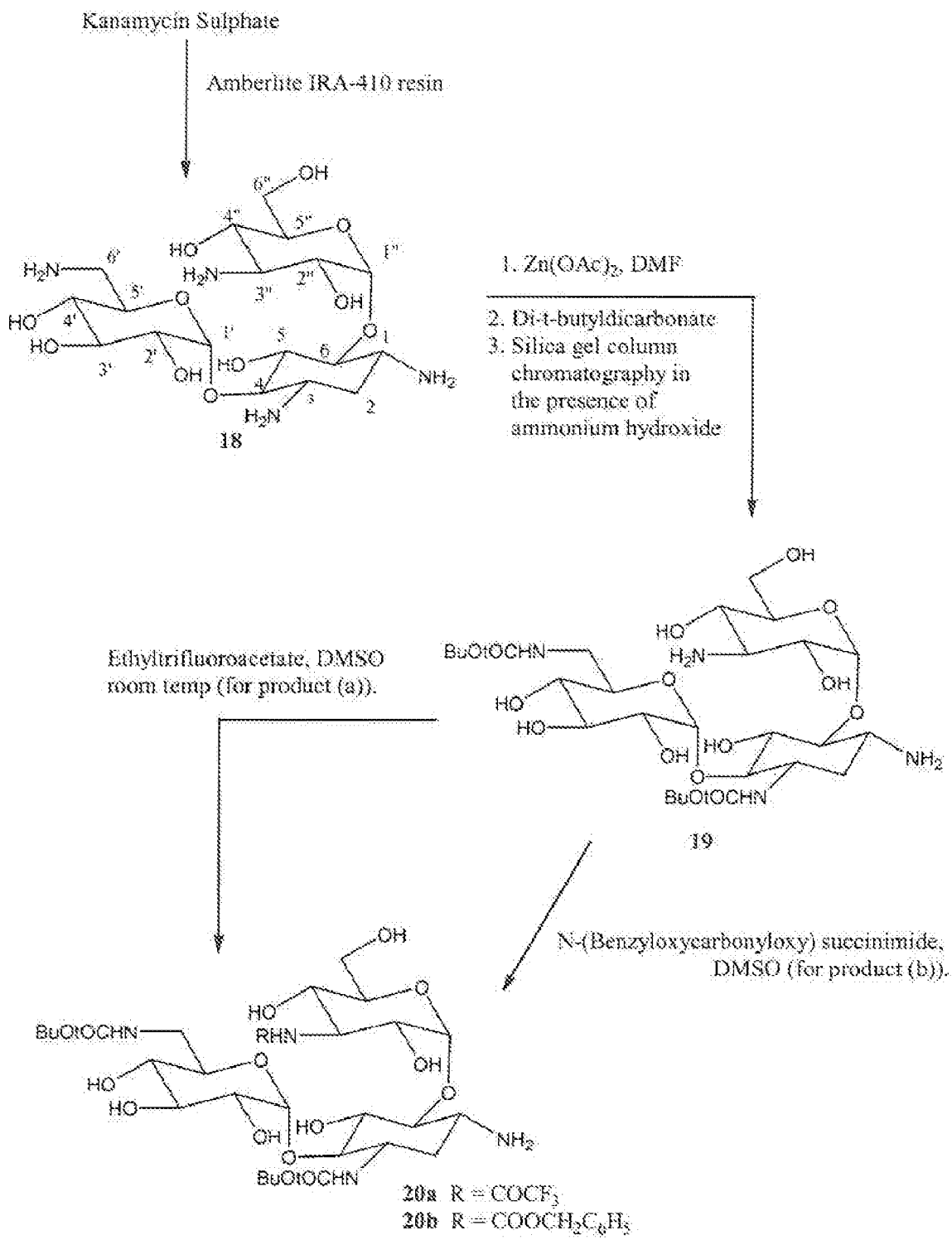
FIG. 11 is a reaction scheme for the selective protection of kanamycin.

Synthesis of Protected Kanamycin (FIG. 11)

Kanamycin A (free base) (18). Kanamycin sulfate (20.0 g) was dissolved in 200 mL of water. This was loaded on a column prepared with 400 g of AMBERLITE IRA-140 resin (6.4 cm×17.5 cm). The column was eluted with water, and the appropriate fractions were collected and lyophilized to give 18.9 g of kanamycin A (free base) (18).

3,6'-Di-N-(tert-butoxycarbonyl)-kanamycin A (19). To 3.5 g (7.2 mmol) of kanamycin A free base (18) was added 200 mL of anhydrous DMF, and the mixture was stirred for 1 hour at room temperature. The reaction mixture was treated with 6.3 g (28.7 mmol) of zinc acetate dihydrate and allowed to stir at room temperature for 2 days. To the reaction mixture was added 3.17 g (14.5 mmol) of di-t-butyldicarbonate. The resultant mixture was stirred for 3 days and was then concentrated. The residue was purified by silica gel column chromatography using 1:1:0.2 $MeOH:CHCl_3:28\%NH_4OH$ to give 2.1 g (3.07 mmol, 42%) of 19 as a white powder.

3,6'-Di-N-(tert-butoxycarbonyl)-3"-N-trifluoroacetyl-kanamycin A (20a). To 1.78 g (2.6 mmol) of 19 was added 10.7 mL of anhydrous DMSO followed by 313 µL (2.62 mmol) of ethyltrifluoroacetate. The reaction mixture was allowed to stir at room temperature for 18 hours and then concentrated. The residue was purified by silica gel column chromatography using 1:1 $MeOH:CHCl_3$ to give 1.5 g (1.92 mmol, 74%) of 20a.

3,6'-Di-N-(tert-butoxycarbonyl)-3"-N-CBz-kanamycin A (20b). To 116 mg (0.17 mmol) of 19 was added 1 mL of anhydrous DMSO followed by 46 mg (0.19 mmol) of N-(benzyloxycarbonyloxy)succinimide. The mixture was allowed to stir for 2 days and was then concentrated. The residue was purified by silica gel column chromatography using 6:4 $CHCl_3:MeOH$ as an eluent to give 70 mg (0.085 mmol, 51%) of 20b.

Example 7

Figure 12:
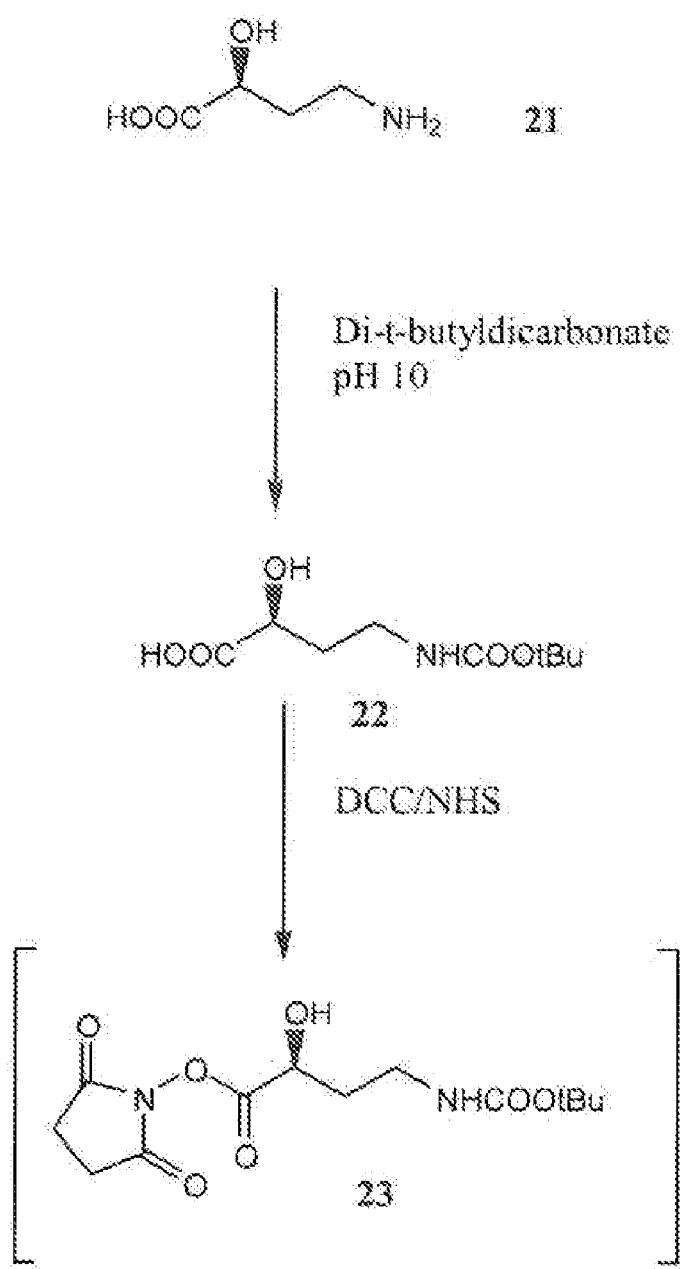
FIG. 12 is a reaction scheme for the in situ synthesis of an active N-hydroxysuccinimide.
Figure 13:
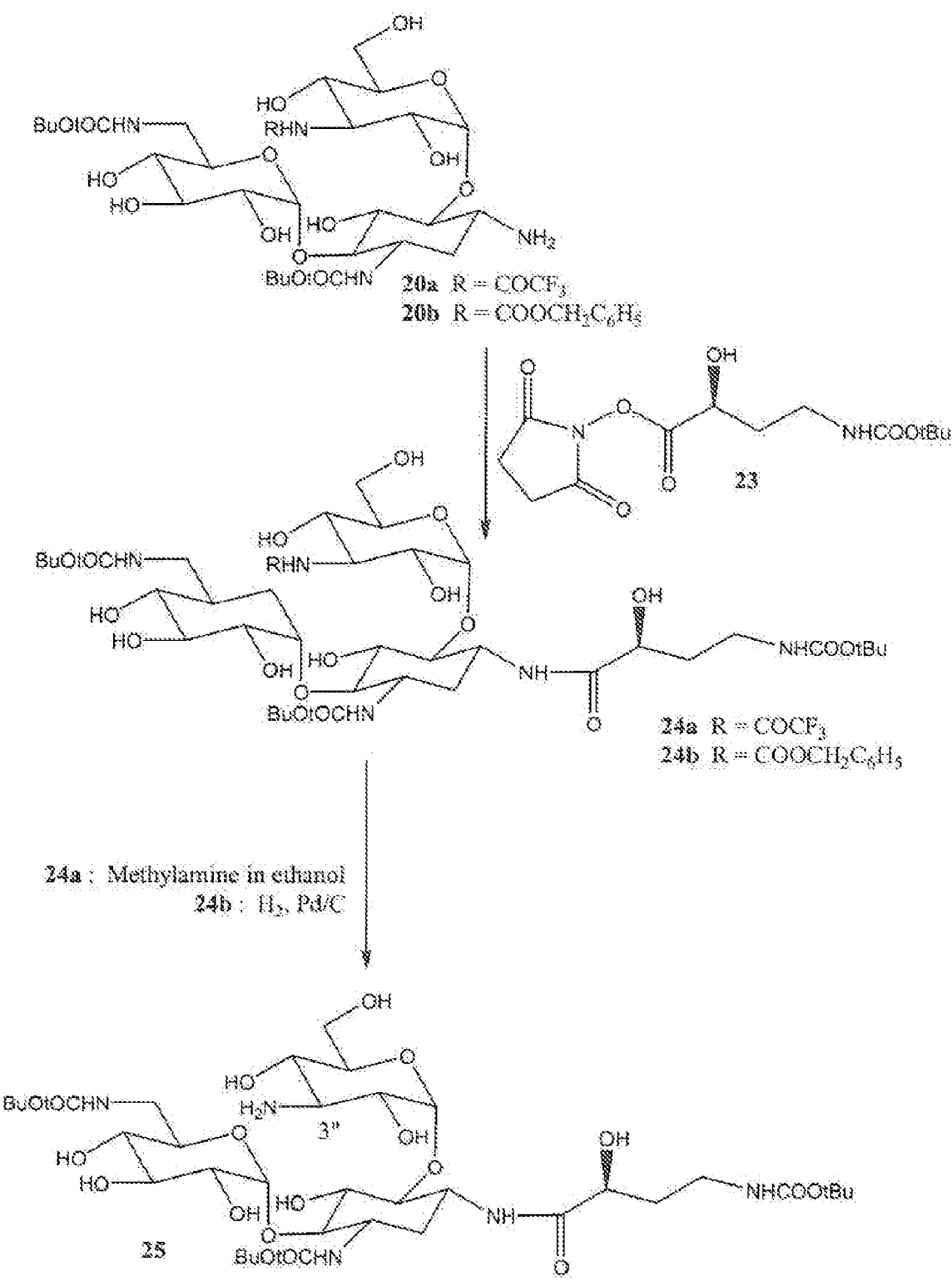
FIG. 13 is a reaction scheme for the synthesis of selectively protected amikacin.

Synthesis of Protected Amikacin (FIGS. 12-13)

S(-)4-N-(tert-butoxycarbonyl)-2-hydroxybutytric acid (22). To 1 g (8.4 mmol) of S(-)4-amino-2-hydroxybutyric acid (21) was added 20 mL of water, 4 mL of acetone, and a few drops of 10 N NaOH to adjust the pH to 10. To the reaction mixture was added 2.32 g (10.6 mmol) of di-t-butyldicarbonate, and the reaction mixture was stirred for 2 hours. During this period, the pH of the reaction was kept at 10 by addition of 10 N NaOH as needed. The reaction mixture was concentrated to remove acetone as much as possible. To the residue, 30 mL of ethyl acetate and 30 mL of water were added. The organic phase was separated, and the aqueous phase was adjusted to pH 2 and then extracted 3 times with 20 mL of methyl isobutyl ketone (MIBK). This extract was combined with the organic phase, and this mixture was dried and concentrated to give 820 mg (3.74 mmol, 44%) of 22 as a white solid.

1-N-[(S)-4N-(tert-butoxycarbonyl)-2-hydroxybutyryl]-3',6'-di-N-(tert-butoxycarbonyl)-3"-N-trifluoroacetyl-kanamycin A (24a). To 80 mg (0.36 mmol) of 22 was added 3 mL of ethyl acetate (dried over 4° molecular sieves) followed by 0.5 mL of anhydrous DMF. The solution was cooled to 0° C. under an argon atmosphere and then treated with 75 mg (0.36 mmol) of dicyclohexylcarbodiimide and 42 mg (0.36 mmol) of N-hydroxysuccinimide. The reaction was allowed to stir at 0° C. for 0.5 hour and then allowed to stand at 4° C. for 2 days. The dicyclohexyl urea was filtered off, and the active N-hydroxysuccinimide ester (23) prepared in situ was used as follows.

To 284 mg (0.36 mmol) of 20a was added 3 mL of anhydrous DMF and 3 mL of anhydrous DMSO. To this magnetically stirred solution was added the previously prepared active ester (23) prepared in situ, and the reaction mixture was allowed to stir at room temperature for 18 hours. The reaction mixture was concentrated and purified by silica gel column chromatography using 70% $CH_2Cl_2$ in methanol to give 150 mg (0.15 mmol, 42%) of 24a as a white solid.

1-N-[(S)-4N-(tert-butoxycarbonyl)-2-hydroxybutyryl]-3',6'-di-N-(tert-butoxycarbonyl)-3"-N-CBz-kanamycin A (24b). To 294 mg (0.36 mmol) of 20b was added 3 mL of anhydrous DMF and 3 mL of anhydrons DMSO. To this magnetically stirred solution was added the previously prepared active ester (23) prepared in situ, and the reaction mixture was allowed to stir at room temperature for 18 hours. The reaction mixture was concentrated and purified by silica gel column chromatography using 1:1:0.5 $CHCl_3$:MeOH:28% $NH_4OH$ to give 235 mg (0.23 mmol, 64%) of 24b as a white solid.

1-N-[(S)-4N-(tert-butoxycarbonyl)-2-hydroxybutyryl]-3',6'-di-N-(tert-butoxycarbonyl-kanamycin A (25). To 200 mg (0.203 mmol) of 24 a was added 15 mL of a 4 M solution of methylamine in ethanol. The mixture was heated at 60°-65° C. for 1.5 hours, during which time a white precipitate started to form. The reaction mixture was concentrated. The concentrate was treated with 30 mL of dichloromethane and then concentrated. The addition of dichloromethane and concentration procedure was repeated 3 times to give 178 mg (0.201 mmol, 99%) of 25 as a white powder.

Example 8

Figure 14:
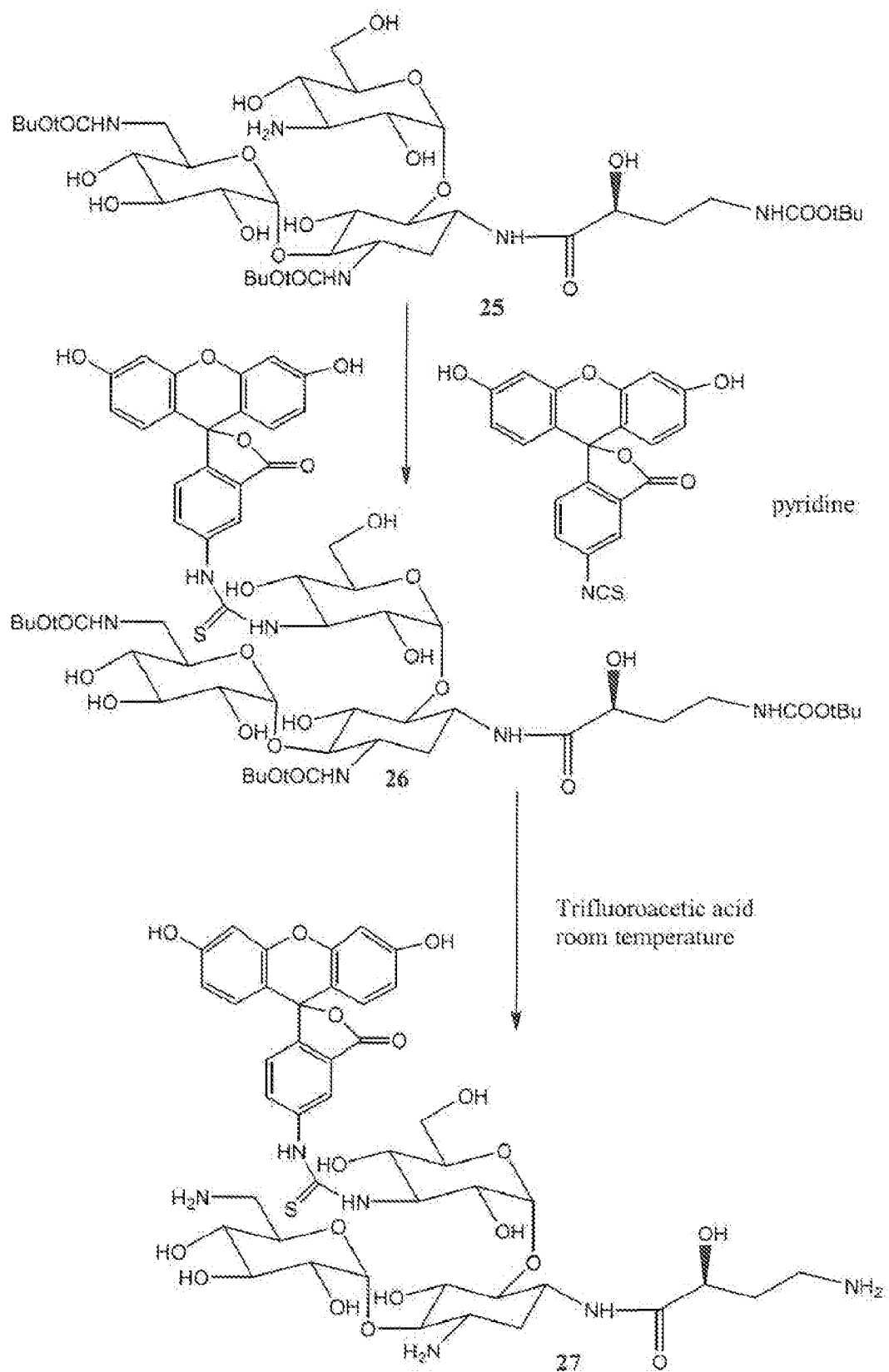
FIG. 14 is a reaction scheme for the synthesis of an FP tracer for amikacin.

Synthesis of Amikacin FP Tracer (FIG. 14)

3,6'-Di-N-(tert-butoxycarbonyl) 3"-N-position-fluorescenyl amikacin (26). To 20 mg (0.022 mmol) of 25 was added 0.5 mL of anhydrous pyridine and 0.5 mL of anhydrous DMF followed by 9 mg (0.023 mmol) of fluorescein isothiocyanate (isomer 1). The mixture was allowed to stir at room temperature for 18 hours and then concentrated. The residue was purified by preparative then layer chromatography using 20% methanol in chloroform to give 15 mg (0.012 mmol, 53%) of 26 as an orange-yellow powder.

Amikacin 3"-N position fluorescein FP tracer (27). To 10 mg (0.008 mmol) of 26 was added 1 mL of trifluoroacetic acid, and the reaction mixture was allowed to stir at room temperature for 5 minutes. The reaction mixture was then concentrated, followed by purification by preparative silica gel chromatography using MeOH:28% $NH_4OH$:$H_2O$ (9:0.5:05) to give 4 mg (0.004 mmol, 53%) of 27 as an orange-yellow powder.

Example 9

Immunoassay Utilizing Amikacin FP Tracer (FIG. 15)

An immunoassay was performed using a COBAS INTEGRA 700 analyzer (Roche Diagnostics Corporation, Indianapolis) using assay reagents and protocols in accordance with the operation manual for the instrument. The instrument was configured for fluorescence polarization measurements for amikacin in serum or plasma sample. The reagent formulation used was the following:
  a) Antibody reagents containing anti-amikacin rabbit antiserum in buffer, pH 7.5, with stabilizer and 0.09% sodium azide (COBAS INTEGRA Amikacin 150 tests, Article 07 3780 1)
  b) FP tracer 27 in buffer, pH 8.0, with stabilizer and 0.09% sodium azide (A 1:50 dilution was made from 0.1 mg/mL of amikacin tracer 27.)
  c) Amikacin calibrator COBAS-FP Amikacin Calibrators Article 07 1762 2US#44541 containing 0, 2.5, 5, 10, 20, and 40 µg/mL (amikacin concentration)

The assay was run on a COBAS INTEGRA 700 analyzer by using 150 µL of the antibody reagent with 25 µL of the calibrator solution and 14 µL of the sample. After completion of the assay, the COBAS INTEGRA 700 calculated the millipolarization units (mp) of the tracer, and a standard curve was generated as shown in FIG. 15. The concentration of drug in the sample can then be determined by comparison to a standard calibration curve.

Example 10

Figure 16:
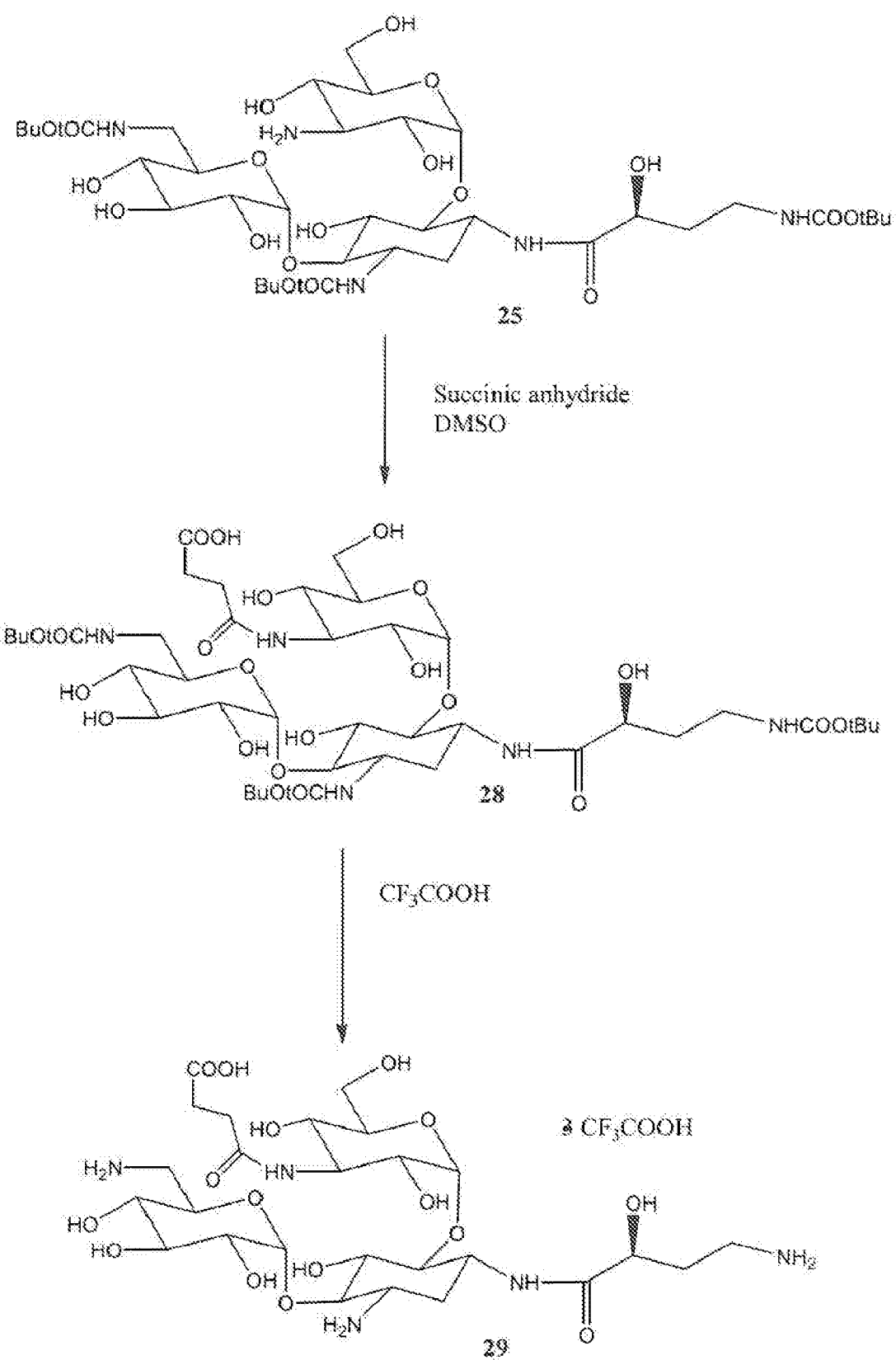
FIGS. 16 and 17 are reaction schemes for the synthesis of amikacin immunogens.
Figure 17:
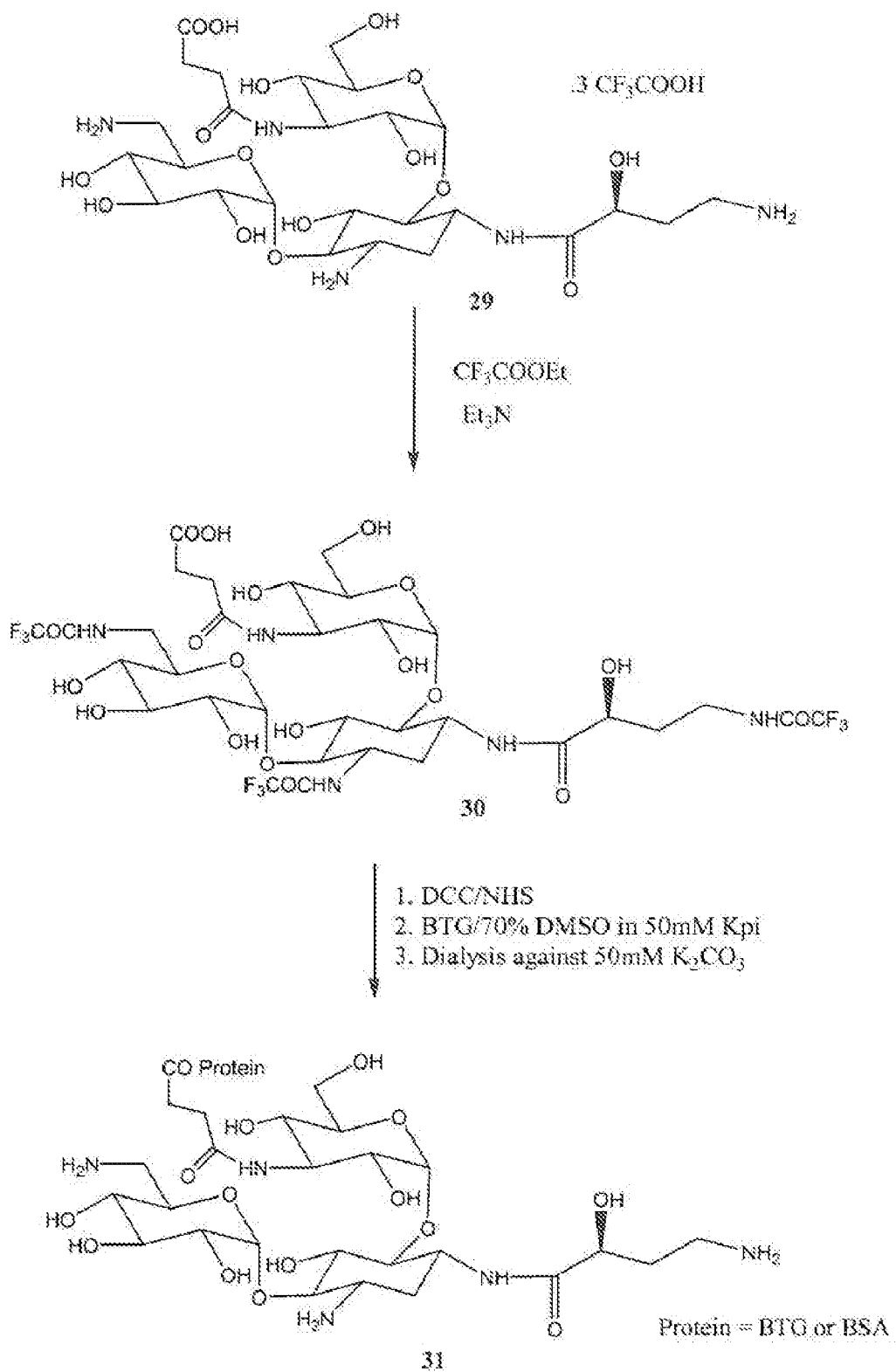

Synthesis of Amikacin Immunogen (FIGS. 16-17)

3,6'-Di-N-(tert-butoxycarbonyl) amikacin 3"N-succinic acid derivative (28). To 120 mg (0.135 mmol) of 25 was added 3 mL of anhydrous DMSO followed by 16 mg (0.16 mmol) of succinic anhydride. The mixture was allowed to stir at room temperature for 3 days under an argon atmosphere and was then concentrated. The residue was purified by silica gel column chromatography using 50% $CHCl_3$ in methanol to give 80 mg (0.08 mmol, 60%) of 28 as a white solid.

Amikacin 3"-N-succinic acid derivative (29). To 30 mg (0.030 mmol) of 10 was added 3 mL of trifluoracetic acid. The mixture was allowed to stir at room temperature for 25 minutes and was then concentrated. The residue was treated with 15 mL of diethyl ether, and the solid formed was isolated to give 20 mg (0.025 mmol, 87%) of 29 as a white solid.

3,6'-Di-N-(trifluoroacetyl)amikacin 3"N-succinic acid derivative (30). To 50 mg (0.064 mmol) of 29 was added 500 µL of anhydrous DMF and 500 µL (3.5 mmol) of triethylamine. Ethyltrifluoroacetate (200 µL, 1.67 mmol) was then added, and the mixture was allowed to stir at room temperature for 18 hours. The reaction mixture was concentrated, treated with 0.5 mL of trifluoroacetic acid, and concentrated. The residue was treated with 5 mL of toluene and concentrated. The addition of toluene and concentration procedure was repeated twice to give 40 mg (0.041 mmol, 64%) of 30.

Preparation of amikacin-BTG conjugate (31). To a solution of 35 mg (0.035 mmol) of the acid 30 in 1.5 mL of anhydrous DMF was added 6 mg (0.05 mmol) of N-hydroxysuccinimide and 8.5 mg (0.038 mmol) of dicyclohexylcarbodiimide. The mixture was allowed to stir at 0° C. for 1 hour and then to stand at 4° C. for 18 hours. The active ester was prepared in situ and used without isolation.

A solution of 150 mg of bovine thyroglobulin (BTG) in 2.5 mL of 50 mM potassium phosphate (pH 7.5) was cooled in an ice-bath. To the solution was added dropwise 9 mL of dimethylsulfoxide, and the reaction was maintained below room temperature. To this protein solution, the previously prepared N-hydroxysuccinimide ester (active ester) solution was added dropwise, and the reaction was slowly stirred at room temperature for 18 hours. The resulting conjugate was placed in a dialysis tube (50,000 MW cut-off) and dialyzed, in order, against 2 L of the following mixtures: 70% DMSO in 50 mM potassium phosphate (Kpi, pH 7.5, room temperature, mixture changed 3 times for treatments of at least 3 hours each), 50% DMSO in 50 mM Kpi (pH 7.5, room temperature, at least 3 hours), 30% DMSO in 50 mM Kpi (pH 7.5, room temperature, at least 3 hours), 10% DMSO in 50 mM Kpi (pH 7.5, room temperature, at least 3 hours), and 50 mM Kpi (pH 7.5, 4° C., mixture changed 4 times for treatments of at least 4 hours each).

The trifluoroacetamido groups of amikacin were deprotected by dialysis against 50 mM $K_2CO_3$ (pH 11) for 5 days (5 changes, 2 L each day) at room temperature. This was followed by dialysis against 50 mM Kpi (pH 7.5, 4° C.) with 6 changes for 6 hours, 2 L each. The protein concentration was determined by Biorad Coomassie Blue protein assay performed by a modified Bradford method.

Example 11

Figure 18:
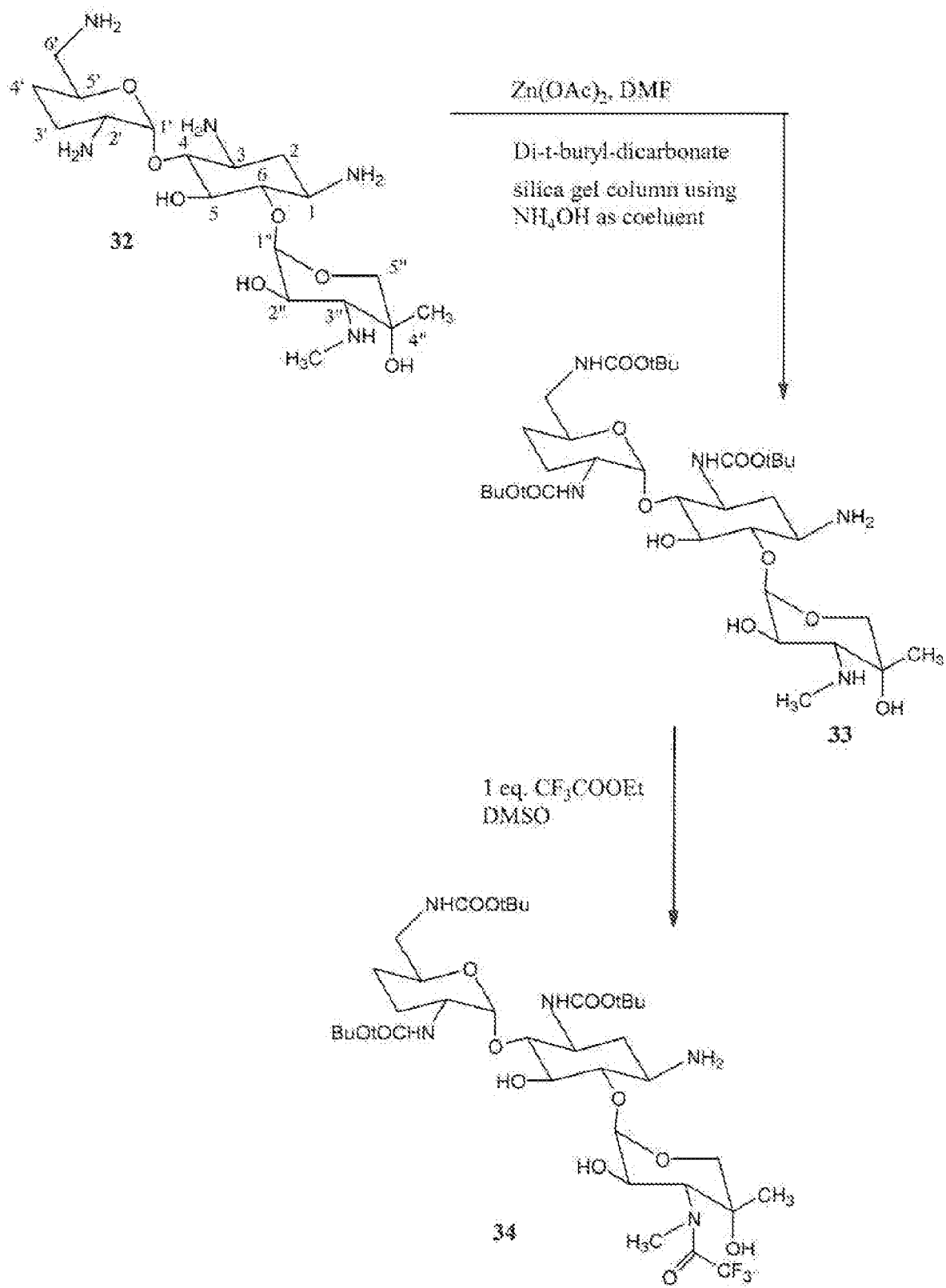
FIG. 18 is a reaction scheme for the selective protection of gentamicin C$_{1a}$.

Synthesis of Protected Gentamicin (FIG. 18)

3,2',6'-Tri-t-butoxycarbonyl gentamicin $C_{1a}$ (33l). To 550 mg (1.22 mmol) of gentamicin $C_{1a}$ (32) was added 35 mL of anhydrous DMF followed by 1.04 g (4.74 mmol) of zinc acetate dihydrate. The mixture was stirred at room temperature under an argon atmosphere for 5 days. To the reaction mixture was added 850 mg (3.89 mmol) of di-t-butyl dicarbonate, and the resulting mixture was stirred at room temperature for 3 days. The reaction mixture was then concentrated under reduced pressure and purified by column chromatography. The crude material was dissolved in a minimum amount of the same solvent used as an eluent in the column. The column was eluted with $CHCl_3$:MeOH:28% $NH_4OH$ (7:3:0.1). The fractions from the column were analyzed by thin layer chromatography (TLC) using the same solvent system used in the column. The plates were developed by dipping the plate in a phosphomolybdic acid solution followed by heating on a hot plate. The retardation factor (Rf) of the product in $CHCl_3$:MeOH:28% $NH_4OH$ (7:3:0.1) was 0.27. The desired fractions were combined and concentrated. The residue was then suspended in 25 mL of dichloromethane and concentrated. The suspension in dichloromethane and concentration procedure was repeated twice more to give 481 mg (0.62 mmol, 51%) of 33 as a white powder.

3,2',6'-tri-t-butoxycarbonyl-3"-N-(trifluoroacetyl)gentamicin $C_{1a}$ (34). To 460 mg (0.602 mmol) of 33 was added 9 mL of anhydrous DMSO followed by 81 µL (0.70 mmol) of ethyltrifluoroacetate. The mixture was allowed to stir at room temperature for 3 days and then concentrated under reduced pressure. During the concentration, the temperature of the water bath was maintained below 45° C. The residue was purified by silica gel column chromatography using a 9:1 mixture of $CHCl_3$ and methanol as eluent. The fractions coming out of the column were analyzed by TLC using the same solvent system. The plates were developed by dipping the plate in phosphomolybdic acid solution followed by heating on a hot plate. The Rf of the product in the 9:1 mixture of $CHCl_3$ and methanol was 0.30. The desired fractions were combined and concentrated. The residue was suspended in 20 mL of dichloromethane and was then concentrated. The suspension in dichloromethane and concentration procedure was repeated twice more to give 480 mg (0.55 mmol, 93%) of 34 as a white powder.

Example 12

Synthesis of Gentamicin-Aminodextran Conjugate (FIGS. 19-21, 31)

1,4-Di-N-hydroxysuccinimide ester of terephthalic acid (35). To 15 g (73.8 mmol) of terephthaloyl chloride was added 300 mL of dichloromethane. The mixture was allowed to stir at 0° C. for 10 minutes under an argon atmosphere. To the reaction mixture was added 30 g (0.26 mol) of N-hydroxysuccinimide followed by the dropwise addition of 30 mL (0.22 mol) of triethylamine at 0° C. The mixture was allowed to warm to room temperature and then stirred at room temperature for 2 days. The solid was filtered off and the residue washed with 200 mL of dichloromethane. The residue was suspended in 300 mL of dichloromethane and allowed to stir for 10 minutes. The solid was filtered and dried to give 24.12 g (66.9 mmol, 91%) of 35 as a white powder.

3,2',6'-Tri-t-butoxycarbonyl-3"-N-(trifluoroacetyl)gentamicin $C_{1a}$-N1 position-aromatic-substituted NHS ester (36). To 64.5 mg of 35 was added 6 mL of anhydrous DMF to produce a di-N-hydroxysuccinimide (di-NHS) ester solution. In another flask was added 64.5 mg (0.17 mmol) of 34, 6 mL of anhydrous DMF, and 128 µL (0.89 mmol) of triethylamine. This gentamicin amine (34) solution was added to the di-NHS ester solution dropwise under an argon atmosphere. The mixture was allowed to stir at room temperature for 48 hours and was then concentrated. The residue was purified by silica gel column chromatography using a 9:1 mixture of ethyl acetate and hexane as eluent. The fractions coming out of the column were analyzed by TLC, detecting the desired product under short wave UV. The Rf of the product in the same solvent system used for the column was 0.36. The fractions containing the product were combined and concentrated, then purified by preparative reverse-phase high performance liquid chromatography (RP-HPLC) using a gradient run. The column used was a RAININ C-18 (ODS) 60° A (21.4 cm×250 mm) with an eluent of water: 0.1% trifluoroacetic acid (TFA) Acetonitrile: 0.1% TFA, with a flow rate of 10 mL/min. The desired fractions were combined, concentrated in a rotary evaporator at room temperature, and then lyophilized to give 49 mg (0.044 mmol, 26%) of 36 as a white powder.

Figure 31:
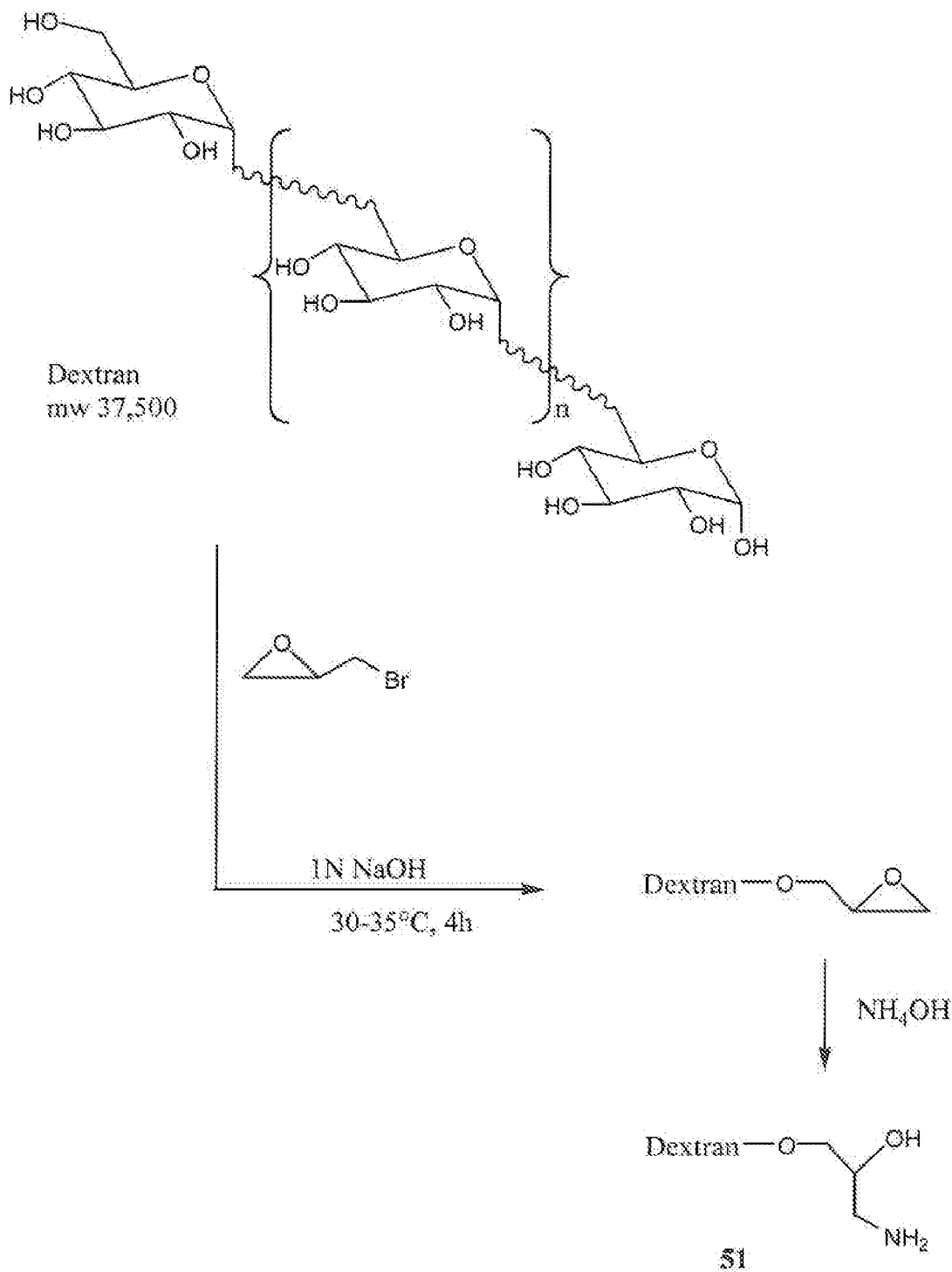
FIG. 31 is a reaction scheme for the synthesis of aminodextran.

Aminodextran (51, FIG. 31). To a three-necked 3-liter flask equipped with a mechanical stirrer was added 700 mL of deionized water. Dextran (70 g, 1.86 mmol) having a molecular weight of 37,500 and obtained from Sigma (Milwaukee, Wis.) was added gradually to the flask while stirring the mixture, dissolving the dextran in the water at room temperature. To the reaction mixture, 140 mL of 1 N NaOH was added, and the reaction was heated to 30°-35° C. A solution of 79 mL (923 mmol) of epibromohydrin in 245 mL of 1,4-dioxane was then added dropwise at 30°-35 °C. over a period of 45 minutes. The resulting mixture was stirred and heated at 30°-35° C. for an additional 4 hours. The reaction mixture was allowed to cool to room temperature and was then transferred to a 2-liter separatory funnel. The organic layer slowly separated as the bottom layer and was discarded. The aqueous mixture was transferred into a 3-liter flask and cooled in an ice-water bath. A solution of 700 mL of 25% ammonium hydroxide was then added to the reaction flask, and the pH was adjusted to 11 with 1 N HCl. The resulting solution was allowed to warm to room temperature overnight. The reaction solution was transferred to dialysis tubing with a molecular weight cutoff of 2,000 daltons and dialyzed in two 12-liter containers according to the following schedule using a total of 20 liters solvent for each step: 1% acetic acid 6 hours, 1% acetic acid for 24 hours, 1% acetic acid for 48 hours, and deionized water for 24 hours (6 times).

The solution was concentrated by rotary evaporation and then lyophilized to give 48 g of produce as a white solid. By using trinitrobenzenesulphonic acid (TNBS) assays, the product was found to contain 5.7 amino groups for every mole of aminodextran (Goldfarb, A. R., *Biochem.* 5, 2570-2574, 1966. See also Snyder, S. L. et. al., *Anal. Biochem* 64, 284-288, 1975).

Gentamicin $C_{1a}$-aminodextran conjugate (38). In a 250 mL Erlenmyer flask was added 500 mg (0.13 mmol) of aminodextran (51). To this was slowly added 50 mL of DMSO at room temperature. The mixture was allowed to stir at room temperature for 10 minutes until all aminodextran went into solution. To this stirred solution, 150 μL (1.08 mmol) of triethyl amine was added. The gentamicin derivative (36) was dissolved in 2 mL of anhydrous DMSO and added dropwise to the stirred aminodextran solution. The mixture was allowed to stir at room temperature for 48 hours. The reaction mixture was transferred into SPECTRAPOR dialysis tubing (MW cut off 2000) and dialyzed (each dialysis using 1 L volume) according to the following schedule: 60% DMSO in 40% deionized water at room temperature (3 times, for at least 3 hours each), 50% DMSO in 50% deionized water at room temperature (2 times, for at least 3 hours each), 30% DMSO in 70% deionozed water (1 time, for at least 3 hours), 10% DMSO in 90% deionized water (1 time, for at least 3 hours), and deionized water at room temperature (6 times, for at least 6 hours each). The solution was taken out of the dialysis tubing and lyophilized to give 430 mg of 37 as a white powder.

To 370 mg of 37 was added 15 mL of dichloromethane. The suspension was allowed to stir at room temperature for 10 minutes. To the reaction mixture was slowly added 15 mL of trifluoroacetic acid, and the resulting reaction mixture was allowed to stir at room temperature for 10 minutes. The reaction mixture was concentrated, and the conjugate was dissolved in 15 mL of deionized water. The reaction mixture was transferred into SPECTRAPOR dialysis tubing (molecular weight cut-off 2000) and dialyzed (each dialysis using 1 L volume) according to the following schedule: deionized water (3 changes, for at least 4 hours each), 50 mM $K_2CO_3$ (pH 11, 5 changes, for at least 12 hours each), and deionized water (4 changes, for at least 4 hours each). The solution was taken out of the dialysis tubing and lyophilized to give 320 mg of 38 as a white powder.

Example 13

Immunoassay Utilizing Gentamicin-Aminodextran Conjugate (FIG. 22)

A conjugate reagent was prepared by making a 240 mM PIPES (piperazinebis(ethanesulfonic acid)) buffer having pH 7.2 and containing 0.1% BSA and 0.09% sodium azide. To this buffer was added conjugate 38 at 0.6 μg/mL to 0.7 μg/mL. Polyacrylic acid was also added at a concentration of 0.8% to 1.0%.

A working reagent was prepared by making a 0.05 M MOPS (4-morpholinepropanesulfonic acid) buffer having pH 7.5, likewise containing 0.1% BSA and 0.09% sodium azide. A microparticle mixture was prepared by mixing equal volumes of a 1% microparticle solution and a 75 μg/mL antibody solution in a 0.05 M MES (4-morpholineethanesulfonic acid monohydrate) buffer having pH 6.4 and containing 0.09% sodium azide. The antibody was from Roche Gentamicin FP kit (COBAS FP Cassett Gent 200 Test, Article 0737844). The mixture was incubated overnight and then washed with a 0.05 M MOPS buffer having pH 7.4 and containing 0.09% sodium azide. A microparticle reagent was then prepared by diluting the microparticle mixture with the working reagent to give a microparticle concentration of 0.15%. The load of antibody on the microparticle was about 0.3 to 0.4 mg/mL.

An immunoassay was performed using an HITACHI 917 automated analyzer (Roche Diagnostics Corporation, Indianapolis) using a 2 μL sample volume, 100 μL of conjugate reagent, and 95 μL of microparticle reagent. The samples assayed were the Roche serum calibrators having concentrations from 0 to 10 μg/mL. The resulting calibration curve is shown in FIG. 22.

Example 14

Synthesis of Gentamicin-Aminodextran Conjugate Precursor (3"N Derivative, FIG. 23)

1,3,2',6'-Tetra-t-butoxycarbonyl-3"-N-(trifluoroacetyl) gentamicin $C_{1a}$ (39). To 60 mg (0.071 mmol) of 34 is added 4.8 mL of a 20:1 mixture of dioxane and methanol followed by 154 mg (0.70 mmol) of di-t-butyldicarbonate. The mixture is allowed to stir at room temperature 30 minutes and then at 40°-50° C. for 30 minutes. The mixture is then concentrated and purified by column chromatography using a 9:1 mixture of $CHCl_3$ and methanol to give the crude product. The crude product is triturated with diethyl ether to give the desired product 39.

1,3,2',6'-tetra-t-butoxycarbonyl-gentamicin $C_{1a}$ (40). To 100 mg (0.0.105 mmol) of 39 is added 7 mL of a 4 M solution of methylamine in methanol. The mixture is heated at 60°-65° C. for 1.5 hours and then concentrated. The concentrate is treated with 30 mL of dichloromethane and then concentrated. The addition of dichloromethane and concentration procedure is repeated 3 times to give the desired product 40.

1,3,2',6'-tetra-t-butoxycarbonyl-gentamicin $C_{1a}$ 1N-aromatic N-hydroxy succinimide ester (41). To 64.5 mg (0.17 mmol) of 35 is added 6 mL of anhydrous DMF to produce a di-NHS ester solution. In another flask is added 150 mg (0.17 mmol) of 40, 6 mL of anhydrous DMF, and 128 μL (0.89 mmol) of triethylamine. This gentamicin amine (40) solution is added to the di-NHS ester solution dropwise under an argon atmosphere. The mixture is allowed to stir at room temperature for 48 hours and then concentrated. The residue is purified by silica gel column chromatography using a 9:1 mixture of ethyl acetate and hexane as eluent to give the desired product 41. The product 41 can then be conjugated to aminodextran as described for the conjugation of 36 into 38.

Example 15

Figure 24:
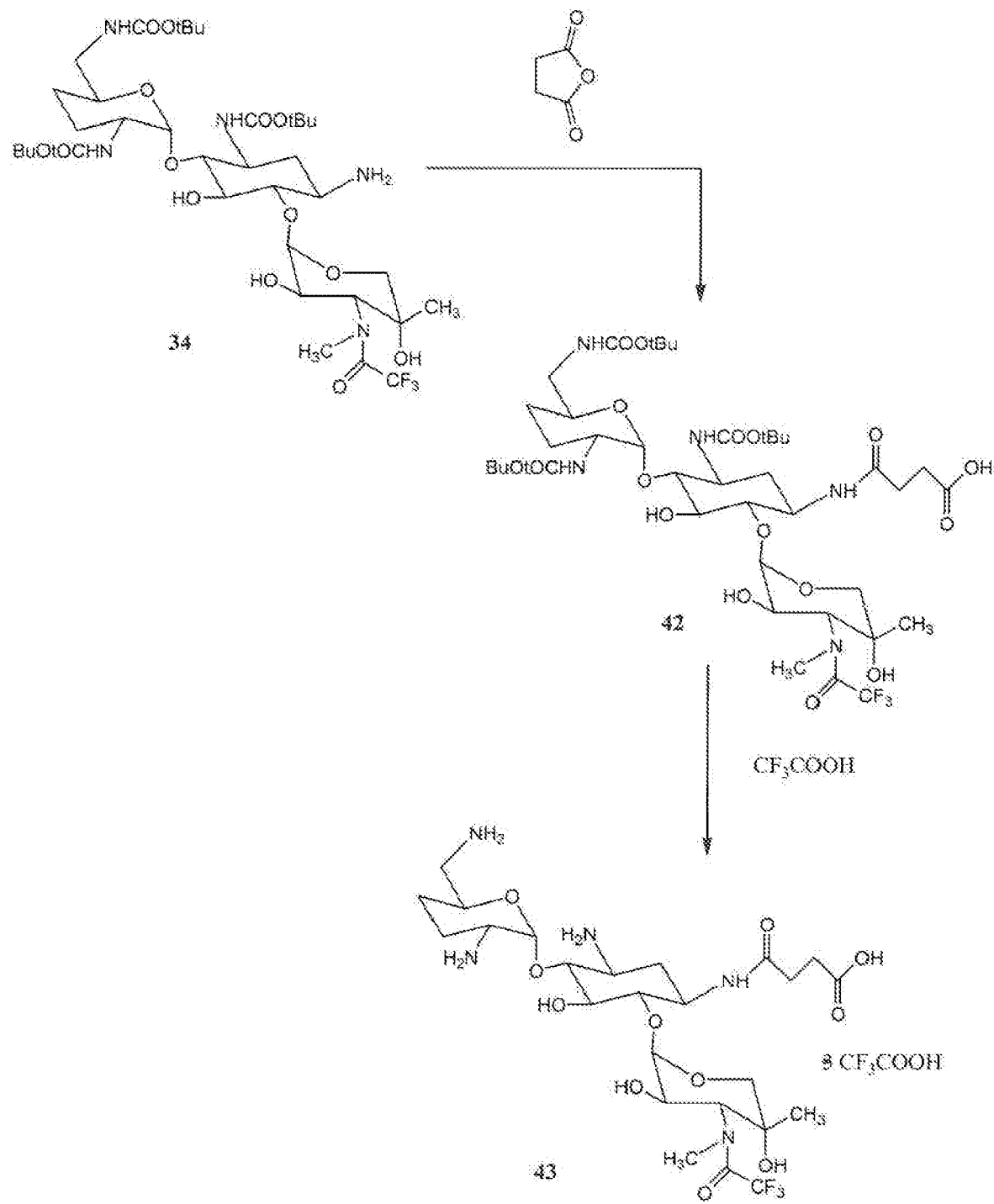
FIGS. 24 and 25 are reaction schemes for the synthesis of a gentamicin immunogen.
Figure 25:
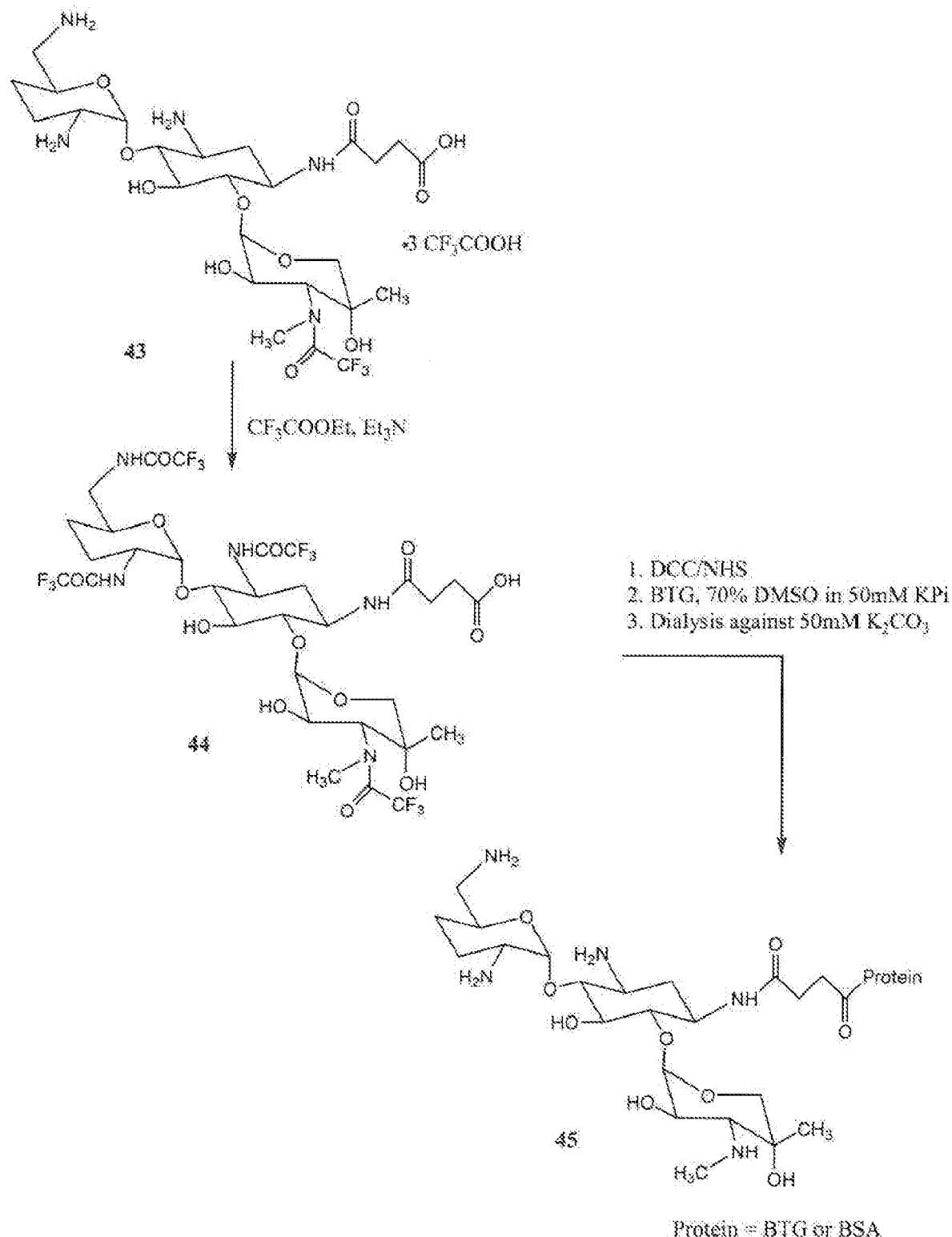

Synthesis of Gentamicin-Protein Conjugate (FIGS. 24-25)

3,2',6'-tri-t-butoxycarbonyl-3"N-trifluoroacetyl gentamicin $C_{1a}$ 1N-succinic acid (42). To 100 mg (0.12 mmol) of 34 is added 2 mL of anhydrous DMSO and 14 mg (0.14 mmol) of succinic anhydride. The mixture is allowed to stir at room temperature 18 hours, then 35 mg (0.34 mmol) of succinic anhydride is added followed by stirring at room temperature for 72 hours. The reaction mixture is concentrated and the residue purified by column chromatography to give the desired product 42.

3"N-trifluoroacetyl-gentamicin $C_{1a}$ 1N-succinic acid (43). To 50 mg (0.052 mmol) of 42 is added 1 mL trifluoroacetic acid followed by stirring for 15 minutes. The reaction mixture is then concentrated. The concentrate is treated with 10 mL of dichloromethane and concentrated. The addition of dichloromethane and concentration procedure is repeated two times to give the desired produce 43.

3,2',6', 3"N-tetrakis-trifluoroacetyl gentamicin $C_{1a}$ 1N-succinic acid (44). To 50 mg (0.050 mmol) of 43 is added 500 μL of anhydrous DMF and 500 μL (3.5 mmol) of triethylamine. This reaction mixture is then treated with 157 μL (1.31 mmol) of ethyltrifluoroacetate and allowed to stir at room temperature for 18 hours. The reaction mixture is concentrated, treated with 0.5 mL of trifluoroacetic acid, and concentrated again. The concentrate is treated with 2 mL of toluene and concentrated. The addition of toluene and concentration procedure is repeated twice to give the desired product 44.

Preparation of gentamicin-BTG conjugate (45). To a solution of 40 mg (0.042 mmol) of the acid 44 in 1.5 mL of anhydrous DMF is added 6 mg (0.052 mmol) of N-hydroxysuccinimide and 10.6 mg (0.051 mmol) of dicyclohexylcarbodiimide. The mixture is allowed to stir at 0° C. for 1 hour and then allowed to stand at 4° C. for 18 hours. The active ester is prepared in situ and used without isolation.

A solution of 160 mg of bovine thyroglobulin (BTG) in 1.6 mL of 50 mM potassium phosphate (pH 7.5) is cooled in an ice-bath. To the solution is added dropwise 9 mL of dimethylsulfoxide, and the reaction temperature is maintained below room temperature. To this protein solution is added dropwise the previously prepared N-hydroxysuccinimide ester (active ester) solution, and the reaction is slowly stirred at room temperature for 18 hours. The resulting conjugate is placed in a dialysis tube (50,000 MW cut-off) and dialyzed, in order, against 2 L of the following mixtures: 70% DMSO in 50 mM potassium phosphate (Kpi, pH 7.5, room temperature, mixture changed 3 times for treatments of at least 3 hours each), 50% DMSO in 50 mM Kpi (pH 7.5, room temperature, at least 3 hours), 30% DMSO in 50 mM Kpi (pH 7.5, room temperature, at least 3 hours), 10% DMSO is 50 mM Kpi (pH 7.5, room temperature, at least 3 hours), and 50 mM Kpi (pH 7.5, 4° C., mixture changed 4 times for treatments of at least 4 hours each).

The trifluoroacetamido groups of amikacin are deprotected by dialysis against 50 mM $K_2CO_3$ (pH 11) for 5 days (5 changes, 2 L each day) at room temperature. This is followed by dialysis against 50 mM Kpi (pH 7.5, 4° C.) with 6 changes for 6 hours, 2 L each. The protein concentration is determined by Biorad Coomassie Blue protein assay performed by a modified Bradford method.

Example 16

Figure 26:
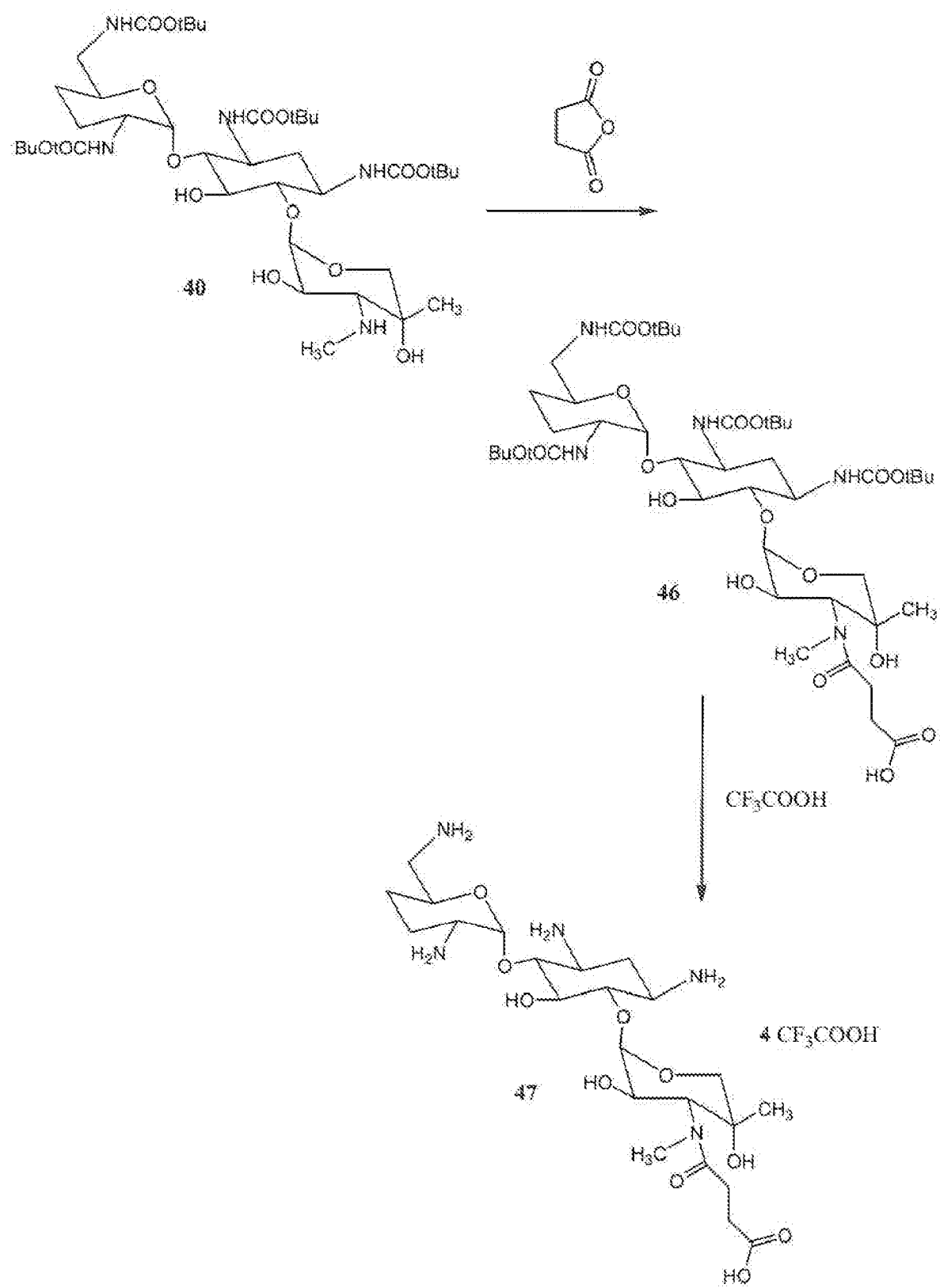
FIGS. 26 and 27 are reaction schemes for the synthesis of a gentamicin immunogen.
Figure 27:
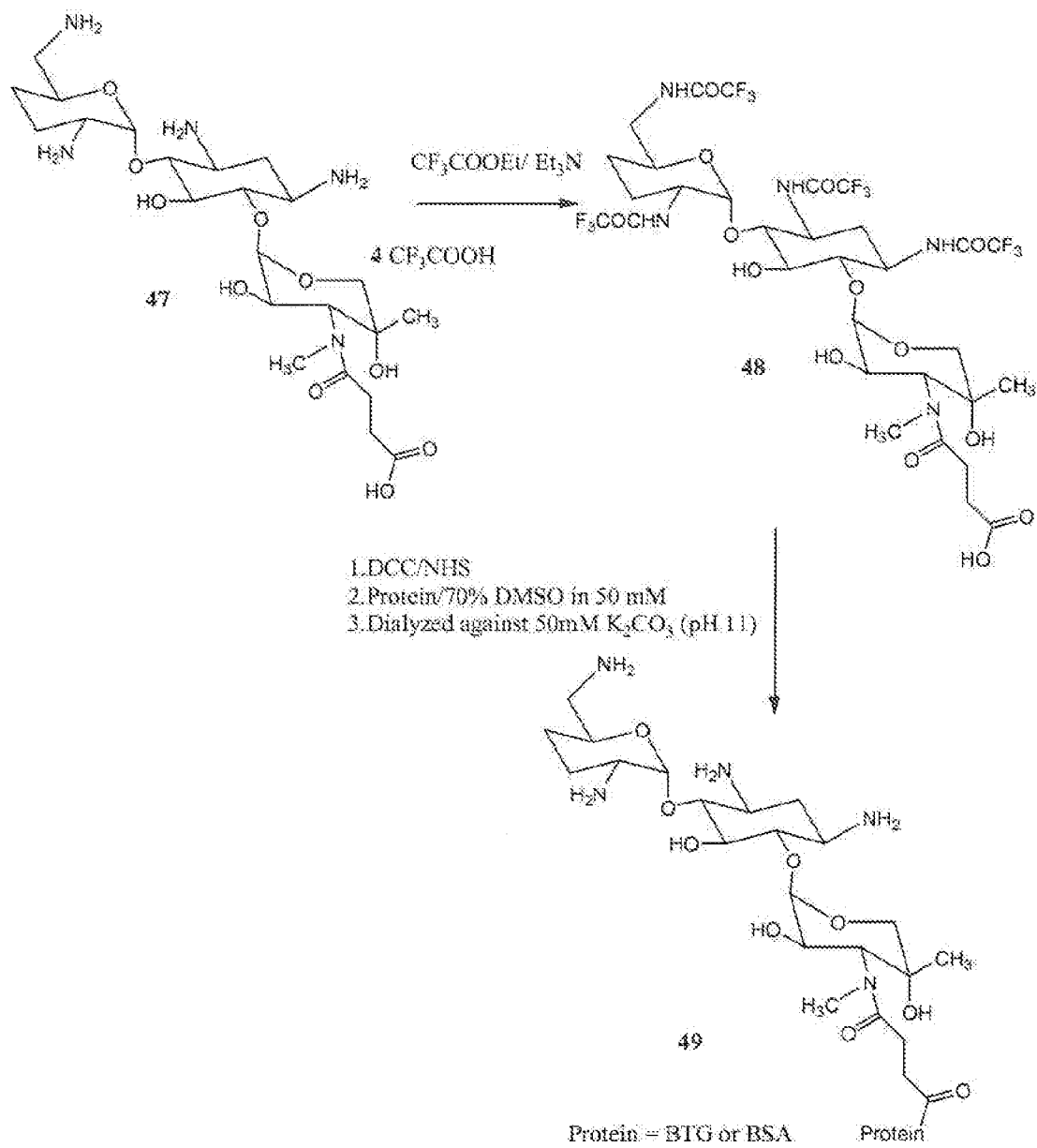

Synthesis of Gentamicin-Protein Conjugate (3"N Derivative, FIGS. 26-27)

1,3,2',6'-N-tetrakis-t-butoxycarbonly gentamicin $C_{1a}$ 3"N-succinic acid (46). To 100 mg (0.117 mmol) of 40 is added 2 mL of anhydrous DMSO and 14 mg (0.14 mmol) of succinic anhydride. The mixture is allowed to stir at room temperature for 18 hours. The reaction is monitored by thin layer chromatography using 20% methanol in chloroform as eluent, which indicates that the reaction is incomplete. This reaction mixture is treated with 35 mg (0.34 mmol) of succinic anhydride and stirred at room temperature for 72 hours. The reaction mixture is concentrated and the residue purified by silica gel column chromatography using 50% $CHCl_3$ in methanol to give the desired product 46.

Gentamicin $C_{1a}$ 3"N-succinic acid (74). To 50 mg (0.052 mmol) of 46 is added 1 mL trifluoroacetic acid, and the mixture is allowed to stir for 15 minutes. The mixture is then concentrated. The concentrate is treated with 10 mL of dichloromethane and then concentrated. The addition of dichloromethane and concentration procedure is repeated two times to give the desired product 47.

1,3,2', 6', 3"N-tetrakis-trifluoroacetyl gentamicin $C_{1a}$3"N-succinic acid (48). To 50 mg (0.049 mmol) of 47 is added 500 μL of anhydrous DMF and 500 μL (3.5 mmol) of triethylamine. This reaction mixture is treated with 157 μL (1.31 mmol) of ethyltrifluoroacetate and allowed to stir at room temperature for 18 hours. The reaction mixture is concentrated, treated with 0.5 mL of trifluoroacetic acid, and concentrated. The concentrate is treated with 2 mL of toluene and concentrated. The addition of toluene and concentration procedure is repeated twice to give the desired produce 48.

Preparation of gentamicin-BTG conjugate (49). To a solution of 40 mg (0.047 mmol) of the acid 48 is 1.5 mL of anhydrous DMF is added 6.5 mg (0.056 mmol) of N-hydroxysuccinimide and 10.8 mg (0.052 mmol) of dicyclohexylcarbodiimide. The mixture is allowed to stir at 0° C. for 1 hour and then to stand at 4° C. for 18 hours. The active ester is thus prepared in situ and used without isolation.

A solution of 160 mg of bovine thyroglobulin in 2 mL of 50 mM potassium phosphate (pH 7.5) is cooled in an ice-bath. The solution is treated dropwise with 9 mL of dimethylsulfoxide, and the reaction temperature is maintained below room temperature. To this protein solution is added dropwise the previously prepared N-hydroxysuccinimide ester (active ester) solution, and the reaction is slowly stirred at room temperature for 18 hours. The resulting conjugate is placed in a dialysis tube (50,000 MW cut-off) and dialyzed, in order, against 2 L of the following mixtures for one day: 70% DMSO in 50 mM potassium phosphate (Kpi, pH 7.5, room temperature), 50% DMSO in 50 mM Kpi (ph 7.5, room temperature), 30% DMSO in 50 mM Kpi (pH 7.5, room temperature), 10% DMSO in 50 mM Kpi (pH 7.5, room temperature, and 50 mM Kpi (pH 7.5, 4° C., solution changed 4 times).

The trifluoroacetamido groups of amikacin are deprotected by dialysis against 50 mM $K_2CO_3$ (pH 11) for 5 days (5 changes, 2 L each day) at room temperature. This is followed by dialysis against 50 mM Kpi (pH 7.5, 4° C.) with 6 changes for 6 hours, 2 L each. The protein concentration is determined by Biorad Coomassie Blue protein assay performed by a modified Bradford method.

What is claimed is:

1. An antibody produced in response to a compound of the formula

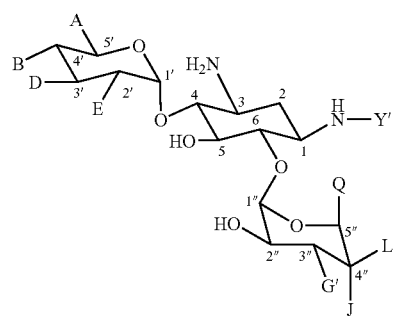

wherein A is $CHCH_3NH_2$; B is H; D is H; E is $NH_2$; G' is $NHCH_3$ or $NCH_3$-T; J is OH; L is $CH_3$; Q is H; Y' is H or T; and T is a carrier, with the proviso that either G' or Y', but not both, comprises T.

2. The antibody of claim 1 wherein the carrier is selected from the group consisting of poly(amino acid)s, polysaccharides, proteins, glycoproteins, and nucleic acids.

* * * * *